US 6,685,058 B2

(12) United States Patent
Redmond

(10) Patent No.: US 6,685,058 B2
(45) Date of Patent: Feb. 3, 2004

(54) FILM FOR DISPENSER PACKAGE IN THE FORM OF A POUCH WITH A FLAP

(76) Inventor: Sanford Redmond, 746 Riverbank Rd., Stamford, CT (US) 09603

( * ) Notice: Subject to any disclaimer, the term of this patent is extended or adjusted under 35 U.S.C. 154(b) by 0 days.

(21) Appl. No.: 10/189,595

(22) Filed: Jul. 8, 2002

(65) Prior Publication Data

US 2003/0071088 A1 Apr. 17, 2003

Related U.S. Application Data

(63) Continuation of application No. 09/717,449, filed on Nov. 20, 2000, now Pat. No. 6,415,939.
(60) Provisional application No. 60/228,434, filed on Aug. 28, 2000, provisional application No. 60/224,654, filed on Aug. 11, 2000, provisional application No. 60/212,977, filed on Jun. 21, 2000, provisional application No. 60/211,865, filed on Jun. 14, 2000, provisional application No. 60/185,779, filed on Feb. 29, 2000, provisional application No. 60/184,512, filed on Feb. 24, 2000, and provisional application No. 60/166,504, filed on Nov. 19, 1999.

(51) Int. Cl.[7] .............................................. B65D 35/08
(52) U.S. Cl. ........................ 222/107; 222/541.9; 383/86
(58) Field of Search ................................ 220/266, 278, 220/275; 215/316; 222/541.9, 543, 107; 383/86

(56) References Cited

U.S. PATENT DOCUMENTS

| 2,226,049 A | 12/1940 | Carley |
| 2,390,822 A | 12/1945 | Wren |
| 2,397,051 A | 3/1946 | Scherer |
| 3,127,085 A | 3/1964 | Hill |
| 3,453,661 A | 7/1969 | Repko |
| 3,788,549 A | 1/1974 | Ostrowsky |
| 4,420,080 A | 12/1983 | Nakamura |
| 4,640,425 A | 2/1987 | Cabernoch |
| 4,770,325 A | 9/1988 | Gordon et al. |
| 4,836,384 A | 6/1989 | Tuns et al. |
| 4,967,910 A | 11/1990 | Schuster |
| 5,779,110 A | 7/1998 | Brown et al. |
| 5,826,737 A | 10/1998 | Zakensberg |
| 6,062,413 A | 5/2000 | Redmond |
| 6,085,941 A | 7/2000 | Pauser et al. |
| 6,244,467 B1 | 6/2001 | Lewit |
| 6,415,939 B1 * | 7/2002 | Redmond .................... 220/266 |

FOREIGN PATENT DOCUMENTS

| DE | 75 33 999 | 5/1977 |
| DE | 93 06 584 | 6/1993 |
| EP | 0 322 980 | 7/1989 |
| GB | 1 592 560 | 7/1981 |
| WO | WO 97/27043 | 7/1997 |

OTHER PUBLICATIONS

Pliant Corp. "Barrier Film Product Guide" (page listing Unilock 242, Unipeel 353, Unipeel 445, Unilon 9006, Unilon 9767).

* cited by examiner

*Primary Examiner*—Phillippe Derakshani
(74) *Attorney, Agent, or Firm*—Kenyon & Kenyon

(57) ABSTRACT

An aperture forming structure for a sealed containment and dispensing package for flowable products is provided. The structure includes a breakaway tip member of thermoformable plastic. In one embodiment a cap may be integrally formed with the aperture forming structure and may be used to protect the tip member or for reclosing the aperture. An alternative embodiment relates to a pouch, wherein a flap member portion of the pouch is folded over and sealingly attached to the body of the pouch. When the flap member portion is pulled away from the body, an outlet aperture is produced through the surface of the pouch.

6 Claims, 41 Drawing Sheets

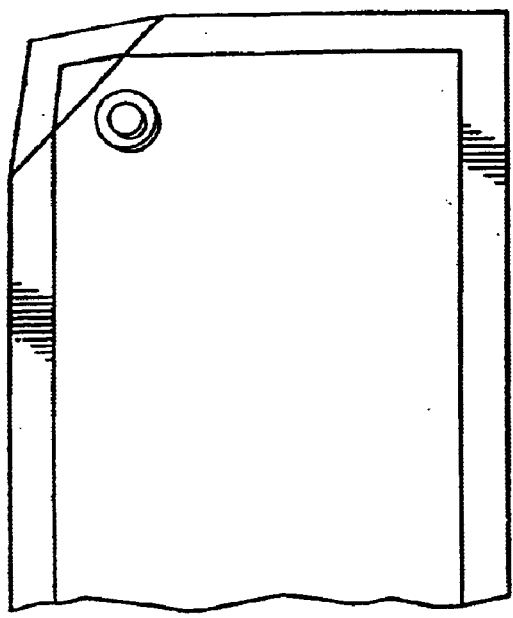 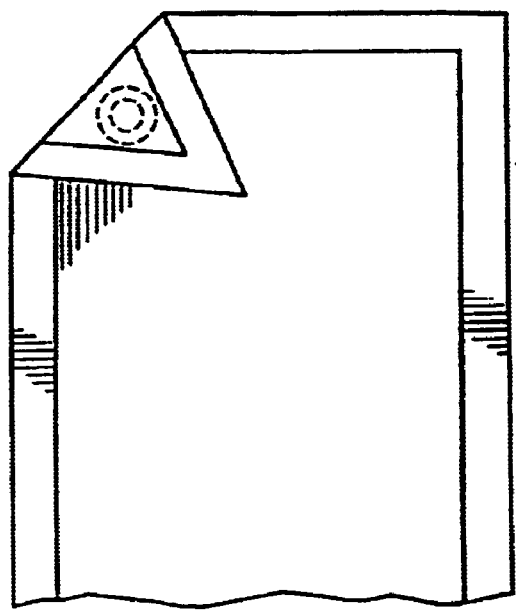
FIG. 56A  FIG. 56B
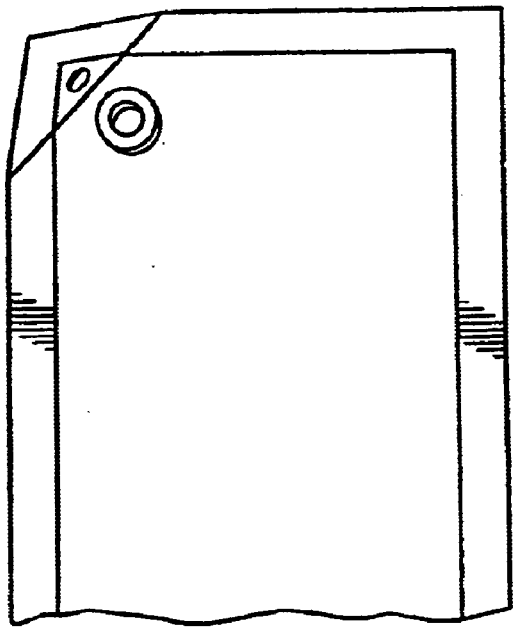
FIG. 56C

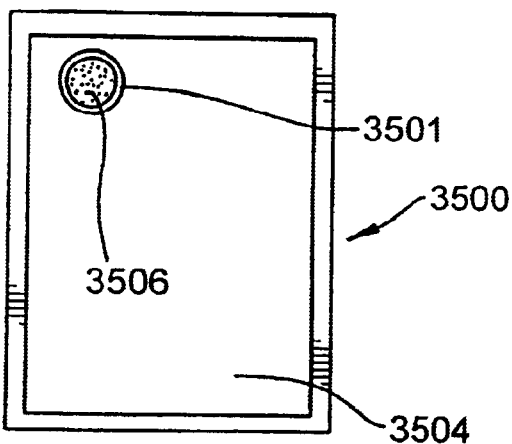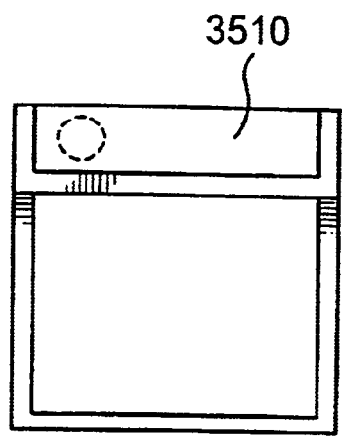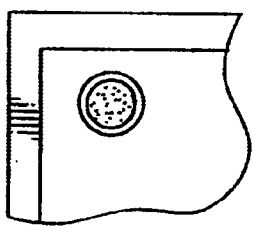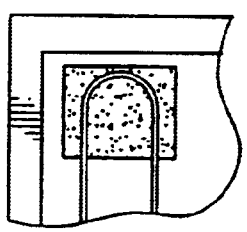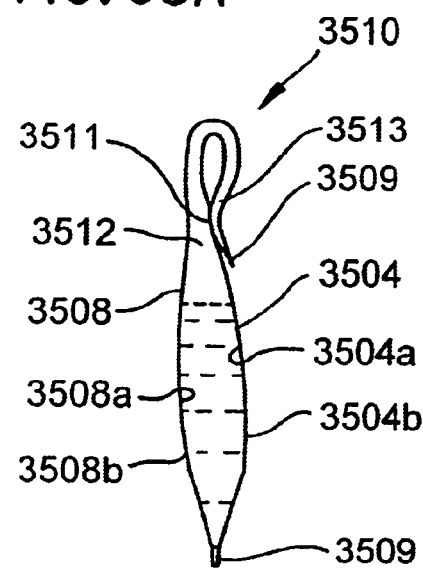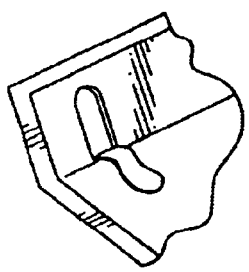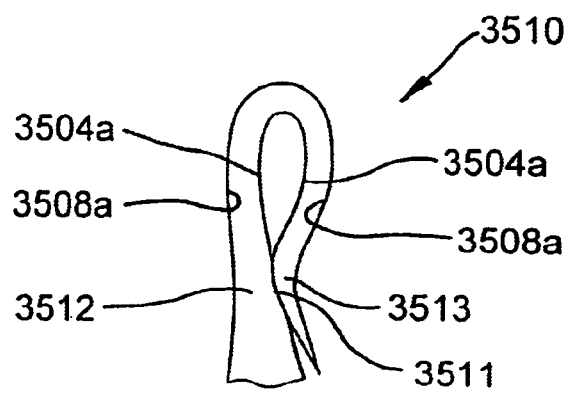

FILM FOR DISPENSER PACKAGE IN THE FORM OF A POUCH WITH A FLAP

This application is a Continuation of application Ser. No. 09/717,449, filed Nov. 20, 2000 now U.S. Pat. No. 6,415,939, which is included herein in its entirety by reference. This application and application Ser. No. 09/717,449 claim benefit of Ser. Nos. 60/166,504, filed Nov. 19, 1999, 60/184,512, filed Feb. 24, 2000, 60/185,779, filed Feb. 29, 2000, 60/211,865, filed Jun. 14, 2000, 60/212,977, filed Jun. 21, 2000, 60/224,654, filed Aug. 11, 2000, and 60/228,434, filed Aug. 28, 2000, which are all included herein in their entirety by reference.

FIELD OF THE INVENTION

This invention relates to easy opening, self-contained, easy to use, single or multiple use dispenser packages capable of economical, high speed production, manufactured from a broad range of materials, many of which are recyclable. They may contain such products as syrups, cream, cheeses, salad dressings, shampoo, hand-cream, liquid detergents, motor oil, toothpaste pates, pet food and many other products. It additionally relates to a package which has the capability of dispensing the contained product, e.g., mouthwash, cough syrup, confections, alcoholic beverages, etc., directly into the mouth of the user, and which also includes a reclosure cap member formed as an integral part of the package and which preferably is tethered to the package by a tether also formed integrally with the package. It will also be seen that the easy opening feature together with the reclosure cap and tether may be formed independently and sealed or adhered to the surface of many packages such as bags, milk containers, pouches, pillow packages (sachets), etc. to make for very efficient low cost dispensing packages or squeeze bags. These squeeze bag type packages could dispense food pastes such as pet food, cremes, grease, yogurt, certain types of dough, cake frosting and could be made of everything from treated, coated paperboard plastic films, foils, laminates or coextrusions of these materials. The easy opening means of this application in its preferred embodiment is comprised of a drum-like protrusion from which a secondary frusto conical protrusion extends to create a tip which is encircled at its base by a fault line. To create the aperture this tip is broken away by applying light lateral finger pressure. In order to protect this breakaway tip during shipment or for reclosing the aperture, a tethered cap is also formed adjacent to the double protrusion. The tether functions not only to hold the cap, thereby preventing the cap from being lost, but also to hold the cap [on the tip] in place by acting like a spring.

In an alternate aperture forming system the initial drum like protrusion has, instead of a frusto-conical breakaway tip, a fault line pattern defined in its top surface, so designed as to rupture to create an outlet of various required shapes when a puncturing tool/plug is pressed into said fault line pattern. Such puncturing tool/plug may be formed instead of a cap and may be tethered or the cap may be double ended with a cap formation on one end and the puncturing tool/plug formation on the other. It will also be seen that a cap containing a protruding member formed within the cap similar to the style of a flower would perform as a central punch when the cap is pressed over the drum shaped protrusion. It will further be seen that in certain instances where a metal foil liner is required for a flowable product such as an alcoholic drink the drum shaped protrusion may be replaced by a moundlike protrusion with a central fault line pattern. The reason for such a moundlike shape instead of the drum shape is to prevent the stretching of the foil beyond its elastic limit at surface intersections in which case it would rupture during formation. Said pattern able to be punched open by a formed puncturing tool/plug said puncturing tool/plug may be thermoformed and tethered to the unit or may be independently made and the tether may have a formed ring at its free end into which the puncturing tool plug may be seated.

This invention also relates to a method and apparatus for manufacturing the aforesaid formation and packaging, reliably at high speed, in many cases from fully recyclable material, so as to permit such packages to be produced at low cost and, in many cases, recyclable. Additionally the packages may use less plastic material than most other previously known portion packages leading to source reduction and environmental benefits even when non-recyclable materials are used.

BACKGROUND OF THE INVENTION

Various attempts have been made to provide a dispenser package in which a product may be packaged in the quantity normally required for single or multiple uses, and from which the contained product may be dispensed.

One type of such dispenser packages is a pillow pouch or sachet, typically made of relatively thin plastics and foils or combinations of laminated plastics and foils. These packages are most frequently encountered as containers for catsup, mustard, other condiments, homecare preparations such as hair conditioners, dyes and cremes, etc. Although this type of package is universally used, it is also universally disliked by the consumer. In order to access the contents, the pouch must be held in one hand while a tearing motion and force are applied by the other hand. Creating the initial tear to break the packages seal is often very difficult, often requiring the assistance of the user's teeth. Moreover, once the initial tear is created, the laminated foil and/or plastic material not only often tears in an uncontrolled fashion, but the holding pressure exerted by one of the user's hands often forces the contents out of the envelope not only before the user is ready to apply the contents, but even before the tearing motion is complete. Opening these packages leads to frayed tempers, broken fingernails, and chipped teeth, as well as other problems. The user must also use both hands to open the container. In the case of invalids, arthritis sufferers and other handicapped people, opening these packages is virtually impossible. Yet another problem associated with these prior packages is the impossibility of efficient reclosure, thereby precluding multiple use of the package, with consequent waste of the unused contents. Further disadvantages include the sachet's inability to function effectively with low viscosity products such as coffee cream, mouthwash or alcoholic beverages, due to the inability of the torn opening to control the direction of flow of such liquids from the package. These packages also are generally totally unrecyclable, and therefore become environmental pollutants. As above-mentioned however, should continued use of these sachets be preferred, then the easy opening feature of this application may be readily and economically adhered to the sachet to make for an easy opening, reclosable, high-barrier package.

Another dispenser package is the peel-top cup used for butter, margarine, syrup, sauces, salad dressing, and other similar products. This type of package requires good eyesight and manual dexterity. Such packages are often used as coffee creamers and have many disadvantages, including difficulty in peeling off the top in order to open, as well as difficulty in pouring, accidental spilling, and the inability to be reclosed so as to preclude more than a single use. Again the inventions described herein can be adhered or integrally formed into these packages to make them easy opening and reclosable. Yet another type of dispenser package is the unsealed corrugated paper package used for salt and/or pepper, which upon bending along an interrupted line cut through the corrugations forms an opening through which the salt or other material contained in the package may flow. These packages only dispense dry, solid flowables with the assistance of gravity, and cannot be used to contain, no less dispense, "wet" or liquid flowable materials. The package of this invention can contain and readily dispense both liquids and dry granular products.

Small, very expensive, metal capped bottles are used for alcoholic drinks and are either poured or consumed directly from the bottle. These bottles may be reclosed, but often are sized for a single drink so they do not have to be reclosed. The instant package can be used for alcoholic beverages at a fraction of the cost of the bottles.

Everyone is familiar with the ubiquitous gable top milk carton and everyone is familiar with the varying degrees of difficulty in opening them. These range from fingernail breaking to just plain unopenable without a knife or other tool.

They never truly reclose and at best are messy and unclean looking. In the U.S. there has been a move toward mounting a screw-on cap combination comprising a threaded nozzle member which is sealed onto one of the slanted gables of s the carton and the other is an unattached screw-on cap. This little injection molded duo is costly to make and to install, possibly on the order of 3 to 5 cents and is commonly used on large gable top juice containers in the half gallon size. These are expensive, high profit items selling for about three dollars each and can bear the extra tariff for the screw-on outlets. There are however billions of these gable top units sold annually for milk and cream in varying sizes from half-pints to half gallons. Producers however are reluctant to increase carton cost significantly and the public continues to use difficult to open cartons.

The instant invention makes available a sealed and tamper evident outlet with a tethered cap, both formed in a single, small plastic unit which can be readily sealed or adhesively attached to the gable over a small pre-made hole. It is ultra low cost and may be made of polypropylene, high density polyethylene, PVC. Polyester etc. utilizing material costing small fractions of a cent. It will be seen that the cap serves a double purpose. It enables the outlet to be reclosed after opening and of equal importance, since the cap is in place over the breakaway tip during shipment it protects the tip from being accidentally hit or subjected to any forces which may open the outlet.

It may be seen that the lower drum-like formation beneath the breakaway tip may be elongated so that when the tip is broken away, an elongated nozzle remains which would allow the flowable substance to be ingested directly from the container or as in the case of motor oil, being poured directly into the engine oil inlet. Another disadvantage currently experienced with dispensing packages is the closing of the outlet opening. Closing the outlet opening of tubes is presently accomplished by means of an injection molded screw-on cap which normally includes a compressible gasketing material. The end of the tube requires a mating thread to match the cap. Both the separately molded gasketed cap and the threaded tube result in increased manufacturing costs. Additionally, the cap, as often as not, is dropped and/or lost while it is being threaded on or off. Furthermore, there has been a growing trend to manufacture such tubes at still greater cost by providing hinged caps with a flat end surface which permits the tube to stand upright. Thus, the cap members currently in use have the disadvantage that they tend to increase the overall cost of manufacture of the dispensing package.

OBJECTS OF THE INVENTION

It is therefore an object of this invention to provide a new and improved means of creating an aperture in a thermo-formable plastic material as well as an integrally formed cap and tether where necessary.

A further object is to form independently such aperture creating means with or without a cap and/or tether for adhesion to other forms of previously difficult to open or non-reclosable packaging.

Another object of this invention is to provide new and improved dispenser packages.

Another object of this invention is to provide a new and improved aperture-forming structure for a dispenser package which allows the user to easily and controllably dispense the contents of the package directly to the user's mouth or in a directionally controlled manner, as desired.

Another object of this invention is to provide a new and improved aperture-forming structure for a dispenser package which opens easily and reliably and yet which can be manufactured economically and at high speed.

Another object of this invention is to provide a new and improved reclosable dispenser package so that the contents thereof may be dispensed in consecutive uses and the outlet opening reclosed between uses.

A further object of this invention is to provide a new and improved reclosable package with an attached cap member formed from the same plastic film which cap member may be thereafter placed over the unopened aperture forming means to protect it and/or to reclose the package after opening.

Another object of this invention is to provide a new and improved reclosable package and removable cap member which may be formed as an integral unit and where the cap member is attached to an integrally made tether and remains attached to the package and which may be placed over the unopened aperture forming means to protect it from changes or accidental opening during shipping and handling.

Another object of this invention is to provide a new and improved reclosable package and tethered cap member which may be formed as an integral unit from a thermo-formable material.

Another object of this invention is to provide a new and improved reclosable package and tethered cap member which may be formed as an integral unit from a thermo-formable plastic material that is recyclable.

Another object of this invention is to provide a new and improved dispenser package and cap member wherein the cap member has an open-ended top of predetermined shape so that, upon placing the cap over the aperture of the package the contents may be dispensed in such shaped stream.

Another object of this invention is to provide a new and improved dispenser package and cap member wherein the cap member includes a utensil device such as tiny protrusions or a flattened surface structure so that the cap member may function as a tool to brush, spread, or otherwise handle the contents dispensed from the package.

Another object of the invention is to replace the cap member with a dual function punch/plug member capable of punching through a tough pre-scored formation to create an aperture and to further act as a plug to close said aperture.

A still further object of this invention is to provide a new and improved method of making a dispenser package embodying the aforesaid features.

Another object of this invention is to provide a new and improved method of thermoforming a dispenser package from a recyclable plastic material at high speed and yet provide a finished package which may be easily and reliably opened by the user.

Another object of this invention is to provide a new and improved apparatus for forming an aperture-forming structure for a dispenser package.

Another object of this invention is to provide a new and improved apparatus for forming a nozzle-like aperture structure in a dispenser package so that, upon opening, the contents of the package may be dispensed in a directionally controllable manner.

Another object of this invention is to provide a new and improved self-centering and self-aligning punch and die apparatus adapted to accurately and reliably form a thermoformable material into a hollow tip-like configuration having a peripherally extending fault line so as to permit the tip to be readily broken away by the user to form an aperture opening through which the contents of the package may be dispensed.

The foregoing specific objects and advantages of the invention are illustrative of those which can be achieved by the present invention and are not intended to be exhaustive or limiting of the possible advantages which may be realized. Thus, these and other objects and advantages of the invention will be apparent from the description herein or can be learned from practicing the invention, both as embodied herein or as modified in view of any variations which may be apparent to these of ordinary skill in the art, the same being realized and attained by means of the parts, constructions and instrumentations, and combinations thereof, as well as in the steps and processes pointed out in the appended claims. The present invention resides in the novel parts, constructions, arrangements, combinations, steps and processes, and improvements, herein shown and described.

SUMMARY OF THE INVENTION

Briefly described this invention is directed to a new reclosable aperture forming means which may be formed with an integrally formed cap member which may be tethered to said aperture forming means to create a unit which may be independently formed and adhesively or sealingly attached to a container wall or surface over a hole in said container wall to create an easy opening, reclosable, when necessary, dispensing package. Said reclosable aperture forming means embodying an integral, hollow protrusion member preferably comprised of two stages, a drum shaped base from which extends a generally conical or frusto-conical tip, said tip member having a fault line encircling it at its juncture with the flat top surface of the first drumlike formation which may be readily broken off to form an opening through which the contents of the package may be dispensed in a directionally controllable stream. After the tip of the protrusion member is broken off by applying light lateral finger pressure, the desired quantity of the contents may thereafter be expelled through the opened nozzle-like outlet by gentle hand squeezing of the package.

In a second embodiment the entire reclosable aperture forming means may be integrally formed into what will become an easy to use reclosable dispensing package. In this second embodiment a generally relatively flexible, compressible pouch or container member is sealably attached to a cover member forming the top or lid of the package. The cover member includes the new reclosable aperture forming means and tethered cap member as described above and similarly used.

In another desirable embodiment the pouch or container member has the integral hollow protrusion and tethered cap member thermoformed into the underside of its relatively stiff rim. The advantage of this version being that the cover member then becomes a relatively thin skinlike member which is very easy to print and less expensive than the formed upper cover member.

The aforesaid cap member which is initially formed with the package as an integral unit is preferably formed along one peripheral edge of either the cover member forming the top or lid of the package relatively closely adjacent to the breakaway protrusion member or on the underside of the rim. A cut line may create a tether member which permits the cap member to be mechanically removed by the user from its molded position in production and placed over the opened nozzle-like aperture forming means so as to protect the breakaway tip during shipping and handling, while remaining tethered to the package. As also preferably embodied, the aforesaid cap member permits the end user of the package to readily open or reclose the package after each use.

In other alternative embodiments of the dispenser package of the present invention:

(i) the breakaway protrusion member forming the aperture in the package may be broken off at the surface of the cover member forming the top or lid of the package, thereby eliminating the nozzle-like outlet configuration in those applications where the contents of the package don't require nozzle formation;

(ii) the cap member may be formed with miniature protrusions to act like a brush, or may have some other desired shape to perform some other desired tool function for use in handling the contents dispensed from the package, such as by brushing or spreading;

(iii) if reclosing the package is not required, the cap member may be open-ended having a predetermined shape such that, upon placing the cap member over the nozzle-like aperture of the package, the contents may be dispensed in such shaped stream;

(iv) the cap member may be provided with an internal central plug dimensioned to mate with the opening formed in the dispenser package to thereby serve as a plug to further ensure sealing of the opening after removal of the breakaway protrusion member; and (v) the breakaway protrusion and tethered cap members may be formed in a portion of the cover member which extends beyond one end of the compressible pouch member at a predetermined angle and communicates with the product contained in the pouch by means of a shallow neck or channel, thereby facilitating application of the contents of the package onto a surface, such as, e.g., toothpaste onto a toothbrush or glue onto a break line. Alternatively, the breakaway protrusion member may be formed in the cover member directly over the pouch portion with the cap formed at an adjacent small flat area. This method yields a somewhat larger pouch volume while using the same total amount of material.

It will be understood that the foregoing preferred embodiments of the dispenser package of the present invention may be thermoformed from a wide variety of plastic materials, including, e.g., PP (polypropylene) Barex, HDPE (high density polyethylene), HIPS (high impact polystyrene) and foamed HIPS, as well as various laminations and/or coextrusions of the aforesaid materials and other plastic materials, including, e.g., PP/EVOH (ethylene vinyl alcohol)/PP; Barex/PP; Barex/EVOH/PP; PET (polyethylene tetrafluoride)/LLDPE (linear low density polyethylene); PET/EVOH/LLDPE; PVC (polyvinylchloride)/LLDPE; NY (nylon)/LLDPE; and NY/EVOH/LLDPE. Alternatively, the aperture forming means and the dispenser packages of the present invention may be formed by injection molding.

It also will be understood that the foregoing preferred embodiments of the dispenser packages of the present invention may be manufactured in a wide variety of sizes, as desired, although the preferred size range is from about 2 ml capacity to about 4 fluid ounce capacity. Similarly, the aforesaid package may be manufactured in a wide range of dimensions. A typical size for a package containing 30 ml or 1 fluid ounce of material is on the order of about 1 inch deep by about 1 inch wide by about 3 to 4 inches long, which fits comfortably in the palm of the hand of most users. Furthermore, the independent formations of aperture forming means and the tethered caps may be applied to a very wide range of packaged from single use sizes to half gallons.

Briefly described, as preferably embodied, the apparatus of the present invention forming the preferred aperture-forming protrusion member in the cover member of the dispenser package includes a two-stage punch member which advances to engage and clamp a thermoformable material against a self-centering and self-aligning hollow anvil member. The first punch member advances to initially form a hollow, drum-shaped protrusion in a specific heated area of the thermoformable material. Thereafter, a second punch member preferably located within, and moveable relative to, the first punch member continues to advance forward. The second punch member includes a first generally frusto-conically shaped surface adapted to form a substantially cylindrical or frusto-conically shaped hollow tip member extending from the drum-like protrusion formed by the first punch member. At the moment formation of the hollow tip member is completed, the forward advancement of the second punch brings a second shallow conical surface into cooperating engagement with the peripheral edge or rim defining the hollow portion of the anvil member to thereby compress the wall of the formed hollow tip about a peripheral portion thereof to create a weakened fault line in the hollow tip protrusion member. As here preferably embodied, the aforesaid punch and anvil members create a fault line at the base of the aforesaid hollow tip protrusion member which extends continuously about the periphery thereof.

In an alternative embodiment of the apparatus of the present invention, the heated sheet of thermoformable material is clamped against the anvil member and a single stage punch member having a generally frusto-conically shaped forward end portion is thereafter advanced to form the aforesaid hollow, substantially cylindrical or frusto-conically shaped tip member. At the moment formation of the hollow tip member is completed, the rim of the anvil member compresses the wall of the hollow tip member about the periphery thereof to create a weakened fault line. It will be seen that the heated thermoformable film (material) may be clamped against a relatively thin plate spaced away from the anvil which contains an accurately aligned hole centered on the aperture of the anvil member. In this embodiment, between the punch and anvil the film will be formed into a conical member as the punch is advanced through the plate and said conical member will then be further formed until it contacts the peripheral edge or rim at the opening of the aperture in the anvil. This alternate apparatus creates a fault line banding or girdling the formed conically-shaped tip member at a predetermined point between its base and its apex.

It will be appreciated by those skilled in the art that the foregoing various brief descriptions and the following detailed description are exemplary and explanatory of the present invention, but are not intended to be restrictive thereof or limiting of the advantages which can be achieved by the invention or various combinations thereof. The accompanying drawings, referred to herein and constituting in part hereof, illustrate preferred embodiments of the invention and, together with the detailed description, serve to explain the principles of the invention.

BRIEF DESCRIPTION OF THE DRAWINGS

FIG. 13a is a schematic elevation view of the breakaway tip formed by the punch and anvil members illustrated in FIG. 12a;

FIG. 21b is a side view of the reclosable outlet aperture forming structure shown in FIG. 21a;

FIG. 24a is a top view of the low profile breakaway tip of FIG. 23a;

FIG. 38a is a front plan view of the outlet forming structure of FIG. 37a;

FIG. 39a is an elevated plan view of the outlet forming structure of FIGS. 37a and 38a;

FIGS. 56a–56c disclose views of the flap of the sachet of FIGS. 55a–55e.

FIG. 64A is a top plan view of a peelable adhesive spot on the front face or wall of a pouch with a laser score line partially encircling a portion of the adhesive spot.

FIG. 64B is an enlarged view of the peelable adhesive spot shown in FIG. 64 with a full circle score line.

FIG. 65A illustrates the pouch shown in FIG. 64 in a frontal elevation with a portion of its top folded over into a flap which brings the encircled adhesive spot into contact with another part of the front face.

FIG. 65B is a side view of the pouch shown in FIG. 65A.

FIG. 65C is an enlarged view of the side view in FIG. 65B with encircled spot sealed to its own front face.

FIG. 66 illustrates an adhesive spot with a tongue shaped score line.

FIG. 67 illustrates the tongue shaped outlet created after the top of the pouch is folded over to create a flap and adhesive is sealed to another part of the front face after which the flap is then raised to open the pouch.

DETAILED DESCRIPTION OF VARIOUS PREFERRED EMBODIMENTS

Referring now more particularly to FIGS. 1–4 and 9 of the accompanying drawings, there is illustrated a dispensing package indicated generally at 10 according to the present invention. The package 10 can be used for single or multiple uses and can be reclosed for further use.

Figure 1:
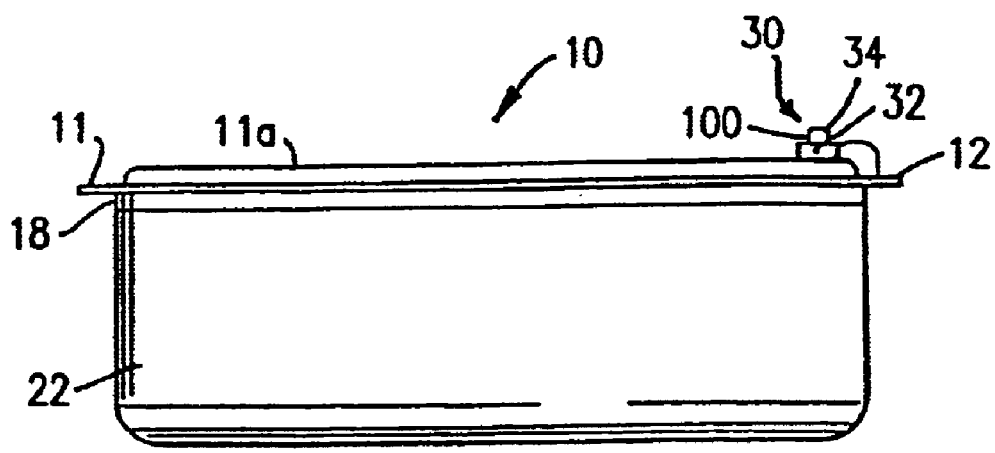
FIG. 1 is a side elevation view of a dispenser package constructed in accordance with the present invention with an integrally formed cap member.
Figure 4:
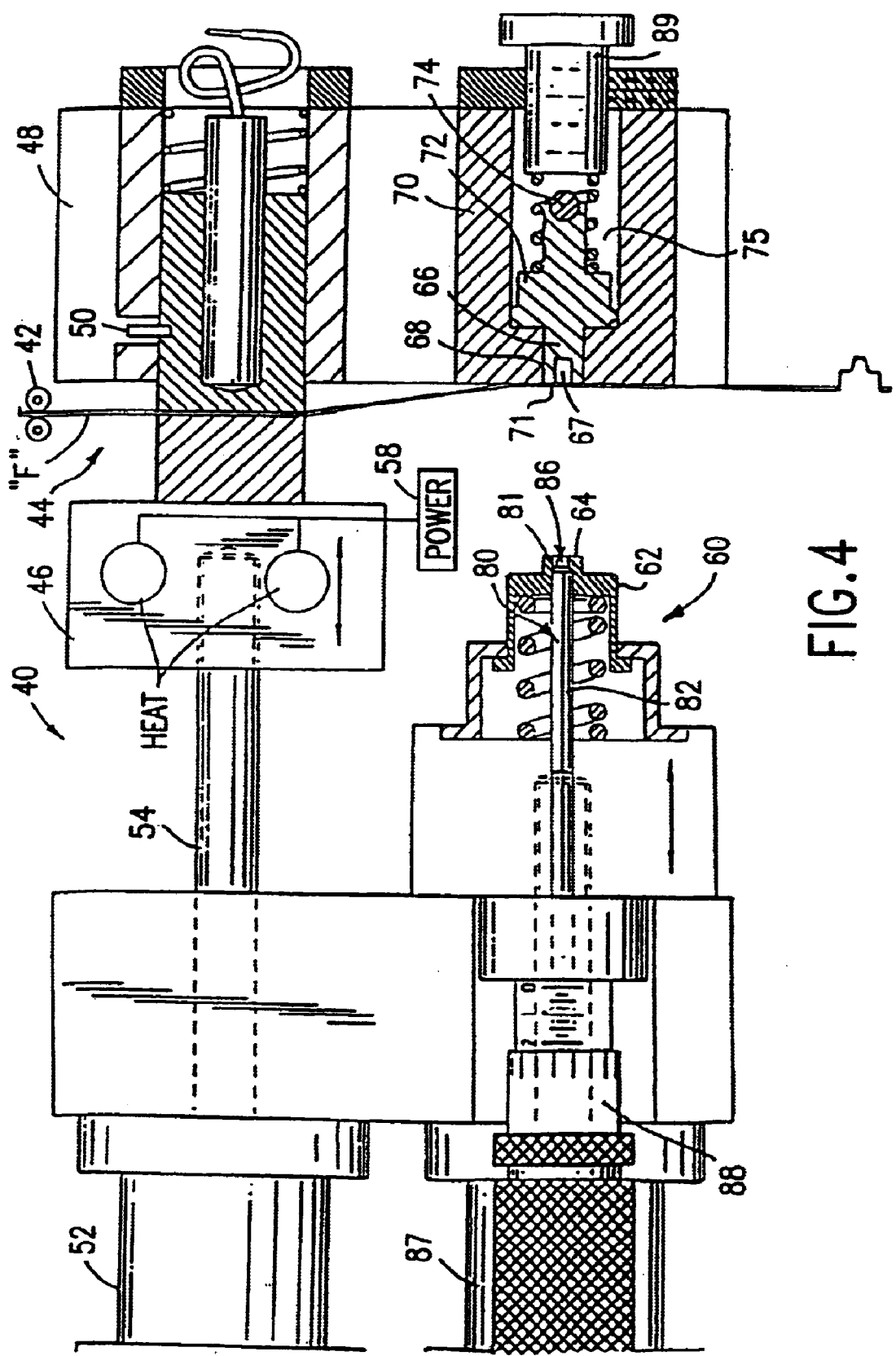
FIG. 4 is a side view in elevation, partly sectional, of an apparatus constructed in accordance with the present invention for forming the breakaway tip and nozzle protrusion members in a heated sheet of thermoplastic material.

As illustrated in FIGS. 1 and 4, the package 10 includes a cover member 11 formed from a flexible but relatively stiff generally flat sheet 12 of a thermoformable plastic material most suitable to the product contained and the protection that the contained product requires.

Materials such as high-impact polystyrene (HIPS), high density polyethylene (HDPE) polyester, HDPE/EVOH (high density polyethylene/ethylene vinyl alcohol), Barex, polypropylene, etc. may be used. HIPS, HDPE, and HPDE/EVOH are each low cost and can be recycled. HDPE/EVOH creates a superior $O_2$ barrier.

As will be understood by those skilled in the art, whereas plastics of similar material may be heat-sealed or bonded together, heat sealing different plastics together requires an adhesive layer. Preferably, linear low density polyethylene (LLDPE) is used as such a layer. Thus, multi-layered plastics formed by coextrusion may be sealed together to form sheet 12 having sealant/barrier 14 of the present invention.

Also suitably bonded to one face of bonded sheet 12, 14 is a flexible sheet 18 forming at least one pouch chamber 22 adjacent one face of the relatively stiff sheet 12 or bonded sheet 12, 14 for containing a preferably flowable substance, e.g. a dry powdered or granulated material or a liquid material of any suitable viscosity capable of flowing under light to moderate hand pressure.

Advantageously, and as here preferably embodied, the layer of a suitable sealant/vapor impervious barrier material 14 is suitably integrally bonded to sheet 12 on the inner surface 16 which faces flexible sheet 18. Flexible sheet 18, advantageously formed by conventional means, such as vacuum forming, pressure forming, mechanical forming or combinations thereof, is likewise suitably integrally bonded to either inner surface 16 or sealant/barrier 14 of sheet 12, as the case may be.

The bonds between substantially flat relatively stiff sheet 12, sealant/barrier material 14 and flexible sheet 18 also may be formed by conventional means known to persons of ordinary skill in the packaging art, such as welding, heat sealing, or adhesive or cohesive bonding. It will be understood that the particular bonding method selected depends upon the particular properties of the materials used and the flowable substance(s) to be contained in the package.

Advantageously, and as preferably embodied, sheet 12 is preferably made of polypropylene (PP), Barex, high impact polystyrene (HIPS) or high-density polyethylene (HDPE), but when combined with barrier 14 may be made of polystyrene, polyester, EVOH (ethylene vinyl alcohol), polyvinyl chloride (PVC), polyethylene tetrafluoride (PET) or nylon, or a copolymer thereof, and barrier 14 is made of a suitable sealant/vapor impervious barrier material, preferably comprising saran and foil laminate, or comprising a laminate of foil and vinyl, or foil alone, depending on the nature of the contents to be contained.

A particularly tough high barrier construction comprises saran laminated on each side with polyethylene (sold by Dow Chemical Co. under the name "Saranex") as barrier sheet 14, in turn laminated onto polystyrene or polyester, forming the flexible but relatively stiff sheet 12. The thickness of sheet 12 varies according to factors, such as the properties of the materials used, the flowable substance contained, and the intended usage. A generally utilized range is 4–12 mils (0.004–0.012"). As previously noted, sheet 12 preferably is somewhat flexible, although more rigid than the material 18 forming pouch 22, and preferably is stiffened by raised portion 11a formed in cover 11 in the preferred construction of package 10.

It will be understood by those of ordinary skill in the art that the bonds formed between materials 12, 14 and 18 can be obtained by the conventional means previously described, again depending on the nature of the flowable substance being contained.

Figure 2:
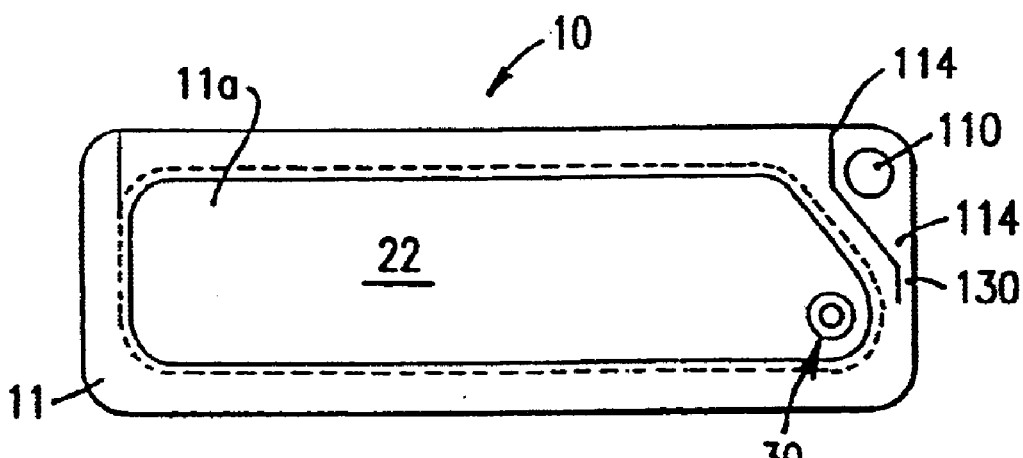
FIG. 2 is a top plan view of the dispenser package of FIG. 1.

It will be seen from the foregoing that the structure of FIGS. 1 and 2 forms an enclosed pouch or chamber 22 between the flexible sheet 18 and the relatively stiff member 12, 14 in which a preferably flowable substance is contained and from which the contained substance is dispensed.

In accordance with the present invention as preferably embodied, the relatively stiff generally flat sheet 12 forming cover 11 includes an aperture-forming protrusion structure 30 which includes a neck member 32 and a breakaway tip member 34 so that, upon removal of tip 34, neck 32 forms a nozzle-like aperture in package 10 through which the contents may be dispensed in a directionally controllable manner.

Neck and tip protrusions 32, 34 preferably are substantially hollow, substantially cylindrical and tip 34 preferably is substantially cylindrical or frusto-conical. In the preferred embodiment as shown in the plan view of FIG. 3, the aperture-forming protrusion structure 30 is located in cover 11 directly over pouch 22 so that, when opened, nozzle aperture 32 communicates directly with the contents of pouch 22.

In accordance with the present invention, as preferably embodied, dispenser package 10 includes a cap member 110 formed as an integral part of cover 11. Advantageously, cap member 110 is removable from cover 11 along a line.

It will be seen that the cap 110 protects the breakaway tip structure 30 from inadvertently breaking off during shipping and handling prior to use, as well as providing a means to reclose the package after opening, i.e., after the protrusion tip member 34 is broken off. Thus, cap 110 protects the remaining contents of the package after each use, permitting multiple uses. The advantage of the tethered embodiment of the invention is that it costs practically nothing, acts as a side pressure spring to maintain the cap on the neck 32 at the opening, acts as a grasping member to assist removal of the cap for each subsequent use, and prevents loss of the cap before the contents of the package have been fully dispensed and the package is ready to be disposed of. Further details of the cap are explained below.

In practically all cases, however, it is believed preferable to provide the two-stage breakaway tip configuration since the first projecting cylindrical formation 32 acts as a nozzle yielding directionally controllable product dispensation, after the tip, i.e., second protrusion 34, is broken off. Low and medium viscosity flowable products tend to squirt "side-ways" or spurt in non-controllable directions, when passing through an aperture formed in the plane of the cover member. Furthermore, elevating the breakaway tip from the surface of the cover member greatly enhances its ease of use with no practical increase in manufacturing cost.

In use, as here preferably embodied, package 10 preferably is positioned so that pouch or chamber 22 rests in the palm of the hand with the thumb resting on the cover 11. The thumb or finger of the holding hand, or the user's other hand, if desired, may then be used to apply a light finger pressure against the side of protrusion tip 34, i.e., the breakaway tip, thereby causing tip 34 to break off, leaving an open neck or nozzle-like aperture 32.

Once tip 34 is removed and the package thereby opened, the contents of the package 10 may be expelled. This method of use depends on the type of substance contained in the package and where the user would like to place the contents. For example, if the package contains toothpaste, the open nozzle 32 preferably would be placed over a tooth brush, whereupon gentle squeezing of the package 10 will force the toothpaste onto the toothbrush. If the contents of the package are intended to be placed directly into the user's mouth, or the mouth of a patient, such as for oral medicine or mouthwash, the open nozzle 32 then may be placed directly into the mouth and a portion, or all, of the contents may then be directed into the mouth by squeezing the package. When the desired quantity of the contents of the package has been expelled, if some contents remain, package 10 may then be reclosed for future use by placing cap 110 over the open nozzle 32.

As previously mentioned, as here preferably embodied, package 10 further includes a cap 110. While cap 110 may be formed separately from the other elements of package 10, in the preferred embodiment cap 110 is integrally formed with and is at least partially detachable from the relatively stiff sheet 12 forming cover 11, as shown in FIGS. 1–3, 9–10, 15–18, 22–23*d*, 29*a–c*, 32–35, 38–40, and 42–47, for example.

Figure 10:
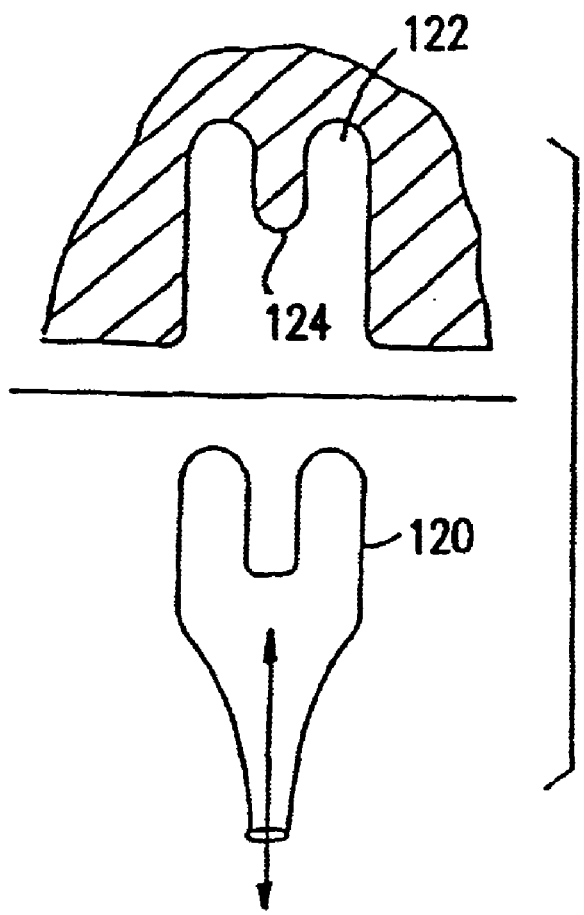
FIG. 10 is a schematic illustration showing the use of a hollow punch member for forming a central sealing plug member in the cap member illustrated in the preceding drawings.

As shown in FIGS. 1–3 and 8–9, cap 110 preferably is located at one corner in cover 11 so as to overhang pouch 22. A cut line 114 allows cap 110 to be easily removed from cover 11. Advantageously, as best seen in FIG. 10, cut line 114 extends only partially along the edge of cover 11 so as to provide a tether 130 to maintain cap 110 attached to package 10 even after the cap is paced over either the aperture-forming structure 30 or over the open nozzle 32.

Cap 110 typically is unthreaded and is dimensioned to fit smoothly, yet securely, over the necked protrusion 32, which preferably also is smooth and unthreaded, both before and after removal of tip 34. Cap 110 has a base 126 which lies flat against the top of cover 11. Tether 130 has several advantages. First, it has been discovered that the tether 130 acts as a spring pressing the cap against the sidewall of the necked protrusion 32, thereby assisting to hold cap 110 in place when it is placed over the necked protrusion 32. Additionally, tether 130 provides the added benefit of preventing the cap 110 from becoming lost and allows the user to grip the tether 130 to assist in removal of the cap 130 from the aperture-forming structure 30 or from open nozzle 32.

Figure 11:
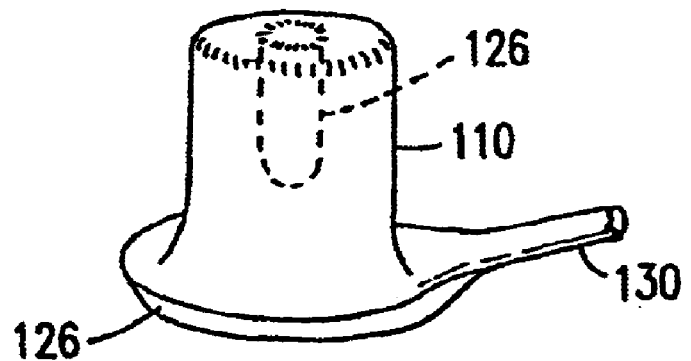
FIG. 11 is an isometric view of a cap member formed with a central plug from the apparatus of FIG. 10.

Cap 110 of the present invention can be designed in several different embodiments. For example, in the embodiment shown in FIGS. 10 and 11, the cap can be formed from a hollow punch member 120 that forces the material into a hollow female member 122 with a central protrusion 124 to form a cap with a central plug 126.

Figure 3:
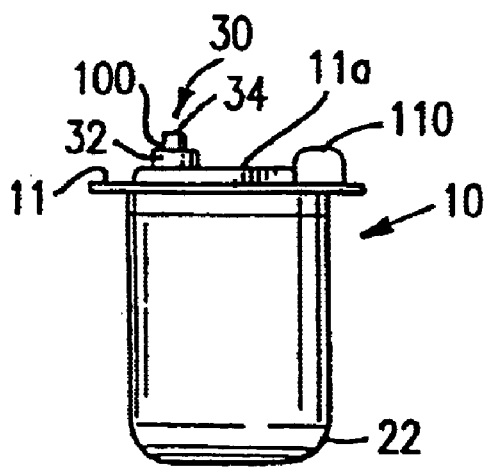
FIG. 3 is an end view of the dispenser package of FIG. 1.
Figure 2A:
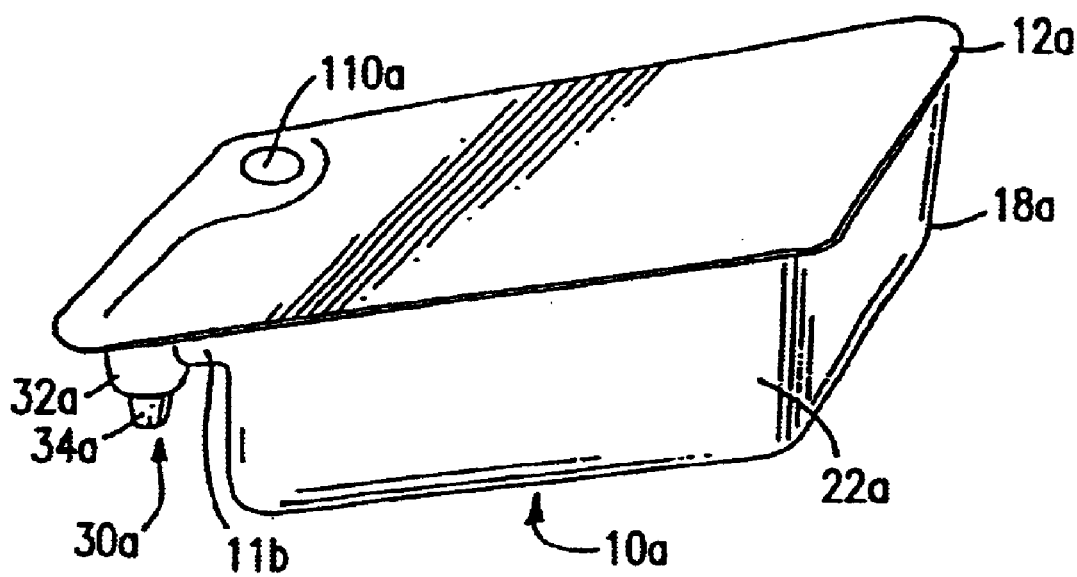
FIG. 2a is a perspective view of a dispenser package constructed in accordance with the present invention with an integrally formed cap member on the underside of the containment members rim and their skin like unformed cover member.
Figure 3A:
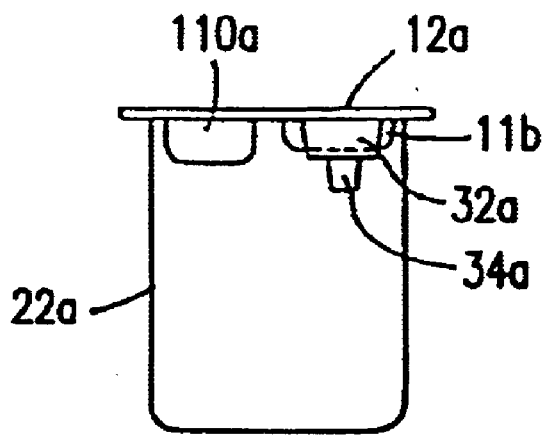
FIG. 3a is an end view of the dispenser package of FIG. 2a showing an unformed very thin flexible cover member.

An alternative to the embodiment shown in FIGS. 1–4 is shown in FIGS. 2*a* and 3*a*. As shown, the container 10*a* has generally the same configuration as container 10 depicted in FIGS. 1–3 is made of the same materials. Specifically, pouch 22*a* is formed between a flexible sheet 18*a* and the very thin skin like sheet 12*a*, 14*a*, in which a flowable substance is contained. Unlike the previous embodiment, the aperture-forming protrusion structure 30*a* is formed on the underside of the flat sheet 18. Similarly, the cap 110*a* is formed on the underside of the sheet 18. With such an arrangement, not only are the neck and tip protrusions 32*a*, 34*a* of the protrusion structure 30*a* protected from accidental rupture, but also the container 10*a* is provided with a low cost flexible cover. In order for the protrusion structure 30*a* to be in fluid communication with the contents of the pouch 22*a*, the pouch 22*a* is provided with a channel 11*b* which communicates with the protrusion structure.

It will be understood that the aperture-forming protrusion structure 30 may be made by a variety of methods and apparatus. In accordance with the present invention, however, as preferably embodied, a web of thermoformable material to be formed into cover 11 is first heated to a sufficient forming temperature. The web is then formed into the hollow cylindrical protrusion 32 with a closed end. The closed end portion of the cylinder 32 is then further deformed in its central section to create the tip 34. At the moment tip 34 is completely formed, the intersection of the base of tip 34 and cylinder 32 is compressed, reducing its thickness, to thereby create a fault line extending about the periphery of the base of tip 34.

Also in accordance with the present invention, as here preferably embodied, aperture-forming protrusion 30 is formed by means of a self-centering and self-aligning male and female punch and die apparatus, indicated generally at 40, as shown in FIGS. 4–7.

Apparatus 40 includes feed rollers 42 or other means to advance the web or film "F" of thermoformable material into a heating station 44 where a heater block 46 advances against the film to press the sheet against a stationary heater block 48, which is temperature controlled by a thermocouple 50 and supplied with necessary power at connection 51. An air cylinder 52 provides the driving force to move the heater block 46 by means of shaft 54. The heater block 46 includes two heaters energized by an appropriate power source 58.

A two-stage punch member 60 includes a first male punch 62 formed as a generally cylindrical hollow punch having a substantially flat end surface 64 at its operative end. When the first punch member is advanced, the end surface 64 engages and deforms the heated sheet of thermoformable, preferably plastic, material F, compressing the plastic against a similarly shaped, oppositely mounted, generally cylindrical hollow anvil member 66 movable in a bore 68 of a support 70. The anvil 66 has an end face 71. The first punch 62 has a clearance fit with the bore 68 so it can be moved therein to confront the end face of the anvil 66. Anvil 66 has an aperture bore 67 formed as part of its hollow portion.

Anvil 66 is part of a spring-loaded rocker member 72, preferably supported by a ball-shaped member 74, or other similarly shaped curved rocker device, in a larger base opening 75 so as to be both resilient and self-centering and self-aligning with punch member 60. Although rocker 74 is preferably curved or ball-shaped, a relatively flat surface in spring-mounted engagement with the base of adjustable mechanism 89 also serves to self-center the aperture opening 67 of anvil member 66 with respect to frusto-conical surface 84 and bevelled surface 83 of second punch 80, more fully described hereinafter. The peripheral edge or rim of aperture 67 in anvil 66 is smaller than the bore of punch 62 to create an internal shoulder 76 when the opposing substantially flat end surfaces 64, 71 of the hollow cylindrical punch member 62 and the anvil member 66 are brought together. The anvil and first punch are preferably made of hardened steel.

Figure 5:
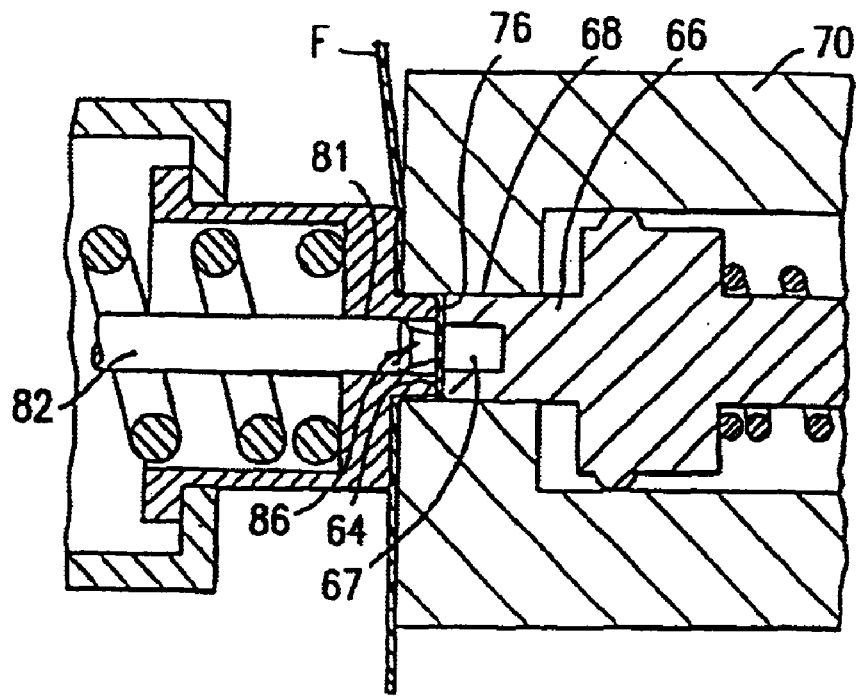
FIG. 5 is an enlarged sectional view, partly in elevation, of the first and second punch members and the self-aligning hollow anvil member illustrated in FIG. 4, this view illustrating formation of the first protrusion member in the thermoplastic sheet material.
Figure 6:
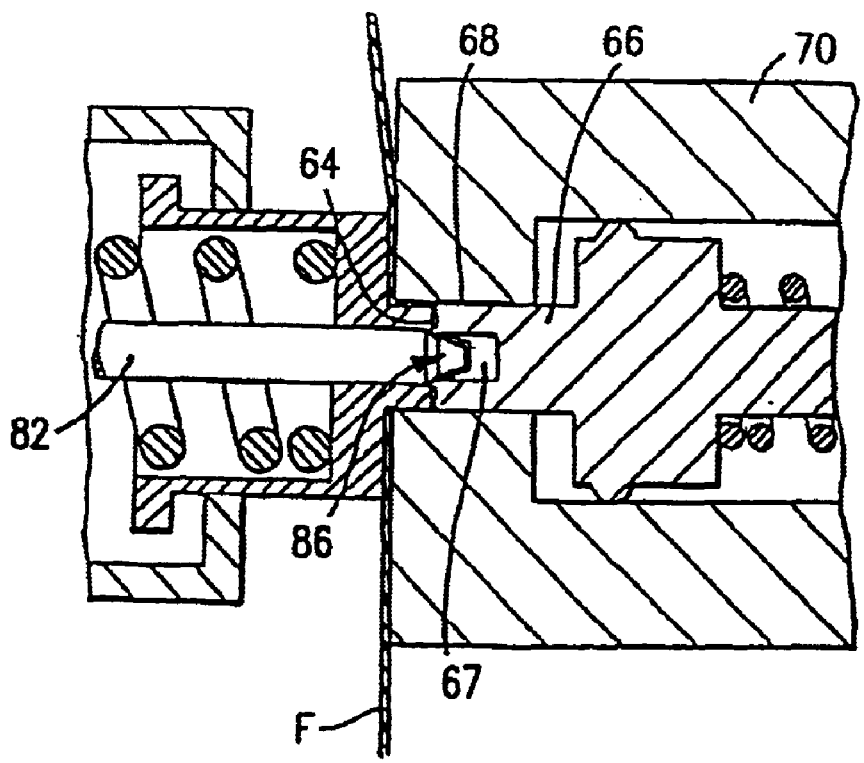
FIG. 6 is an enlarged view similar to FIG. 5, illustrating formation of the second protrusion member in the thermoplastic sheet material.
Figure 8:
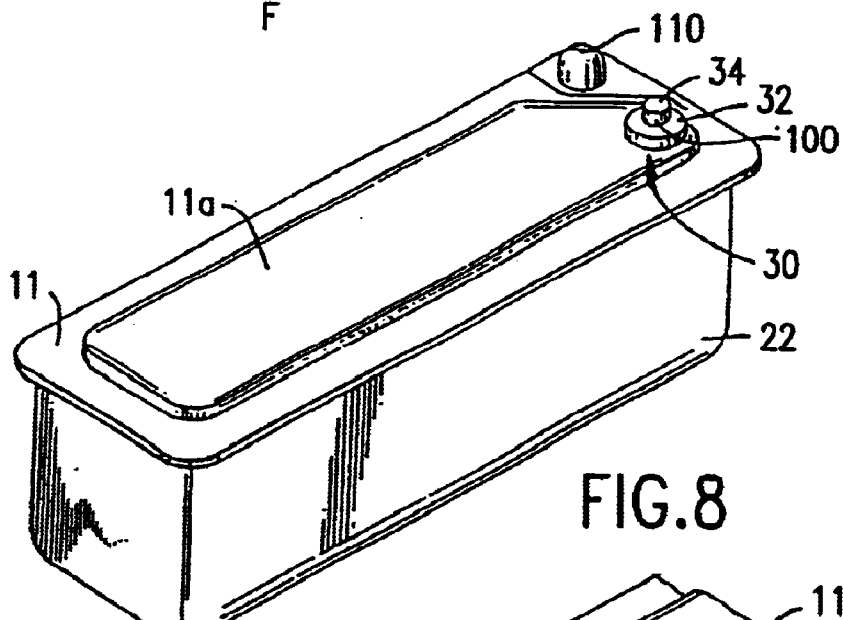
FIG. 8 is an isometric view of the dispensing package of FIG. 1.
Figure 9:
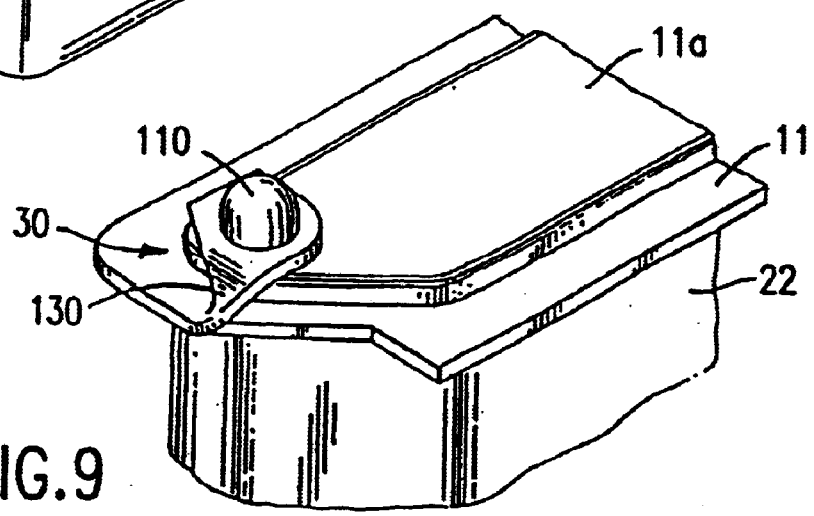
FIG. 9 is an enlarged isometric view of the dispensing package of FIG. 8, illustrating the cap member removed from its molded position and placed over the breakaway tip protrusion member.

In use, at the end of the first stage of the formation of the aperture-forming protrusion 30, shown in FIG. 5, the plastic web F is formed into a projecting, closed end, hollow generally cylindrical drum-like shape, with the plastic web stretched across the end of the first generally cylindrical hollow punch, and clamped between the opposed facing end surfaces 64, 71 of the punch and anvil members.

A second punch member 80 is mounted for travel within a hollow bore 81 and beyond the end face 64 of the first punch member 62. The second punch member 80 includes a shaft 82 whose operative end surface includes a shallow bevel 83, advantageously on the order of 45°, terminating into a conically-shaped portion 84 with a flat end face 85 forming a frusto-conically shaped tip, indicated generally at 86. The second punch member and its bevel 83 advances into controlled engagement with the internal peripheral edge of the shoulder 76 formed at the opposed end surfaces 64, 71 of the first punch 62 and anvil 66.

In one aspect of the present invention, as preferably embodied, the second punch member 80 can be constructed in multiple parts. For example, each of the frusto-conical and beveled portions 84, 83 may be formed separately and removably attached to the leading end surface of the shaft 82, such as by threaded connections. Alternatively, shaft 82 and tip portions 83, 84 may be formed as an integral unit. The second punch member is driven by air cylinder 87.

It will be understood from the foregoing that the full length of the frusto-conical end 86 of punch 80 continues to travel past the formed internal shoulder 76 and into the anvil aperture 67 until such time as bevel surface 83 is brought into accurately controlled cooperating engagement with the internal peripheral edge of the internal shoulder 76 formed by the opposed end surfaces 64, 71 of the first punch 62 and the anvil 66. Advancement of punch surface 83 against shoulder 76 is accurately controlled by micrometer punch adjustment mechanism 88 and anvil adjustable stop mechanism 89.

The still-heated closed end of the initially formed hollow cylinder 32, i.e., the first drum-like protrusion of the aperture-forming structure 30 is, in a second stage, further formed into a substantially cylindrical or frusto-conically shaped tip 34, i.e., the second protrusion of the aperture-forming structure 30, by the advancing second punch member until the shallow bevelled surface 83 of punch 80 engages the plastic sheet. At that time, the second punch surface 83 controllably compresses, cools and sets the plastic web F against the internal peripherally extending edge formed at shoulder 76 of the anvil to reduce the thickness, and thereby weaken, the wall of the plastic at the locus of the peripheral edge so as to form a narrow, peripherally extending indentation 100, known as a rupture or fault line, at the base of tip protrusion 34. It will be seen that fault line 100 permits the tip protrusion 34 to be readily broken away by means of only light lateral pressure to thereby form a nozzle-like outlet opening at neck protrusion 32.

It should be noted that changes in the dimensions of the beveled end 86 and the anvil 66 are within the scope of the present invention. For example, it is often desirable to produce a fine stream of the contents of a container, such as motor oil. Consequently, the opening formed by the base of the tip protrusion 34 must be relatively small, such as shown in FIG. 8a. To form such a aperture-forming protrusion structure 30, the end 86 is elongated, and the beveled surface 83 is positioned closer to the distal end 85. Furthermore, the anvil 66 is provided with a relatively narrow opening. Consequently, as shown in FIG. 7a, the fault line 100 and the breakaway tip 34a are smaller. Alternatively, the entire punch 82 and, therefore, protrusion structure 30 is made narrower.

Figure 7:
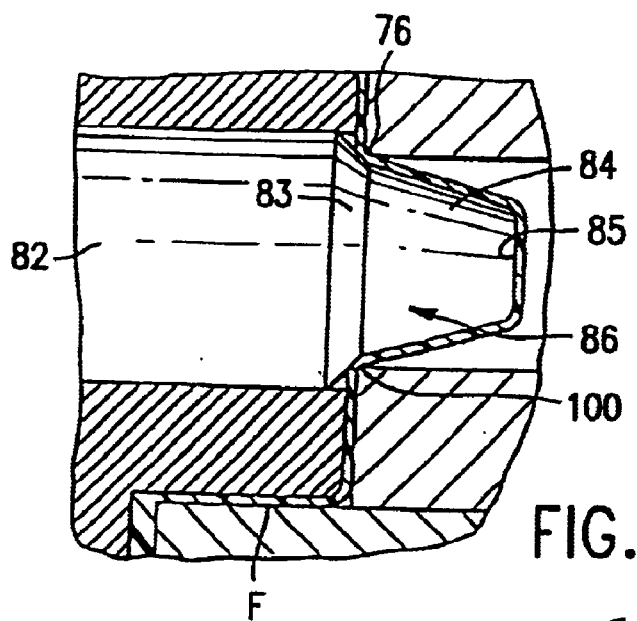
FIG. 7 is an enlarged view of FIG. 6, illustrating formation of the peripherally extending weakened fault line at the base of the second protrusion member.
Figure 7B:
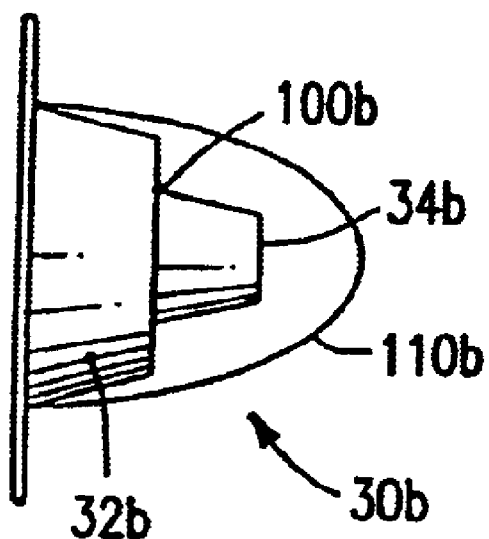
FIG. 7b is an enlarged side plan view of first and second protrusion members according to one embodiment of the present invention.
Figure 7A:
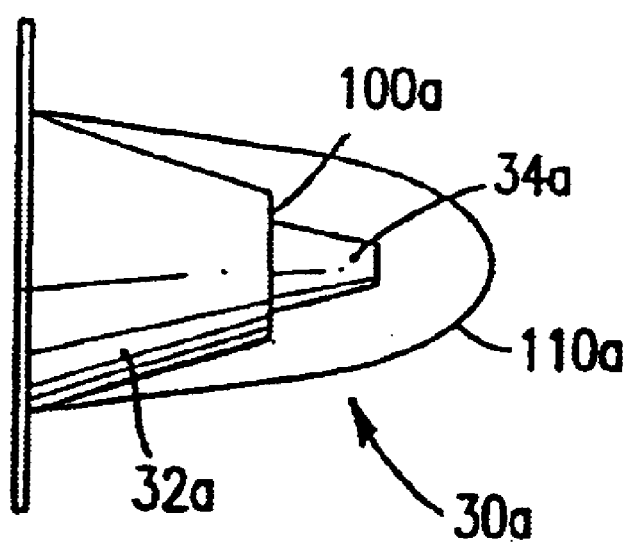
FIG. 7a an enlarged side plan view of first and second protrusion members according to one embodiment of the present invention.

In other applications, where the contents of a container are large particles, such as cat food, the opening must be relatively large, such as shown in FIG. 7b. To achieve a larger opening, the entire punch 82 and, therefore, protrusion structure 30 are made wider. Alternatively, the fault line 100 and the break away tip 34 are made larger.

Figure 13:
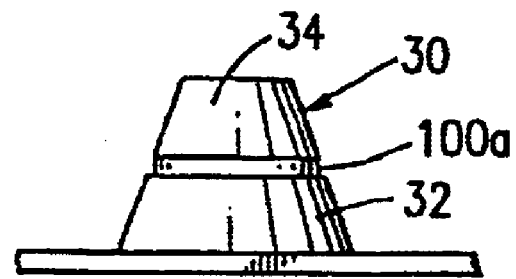
FIG. 13 is a schematic elevation view of the breakaway tip formed by the punch and anvil members illustrated in FIG. 12.
Figure 12:
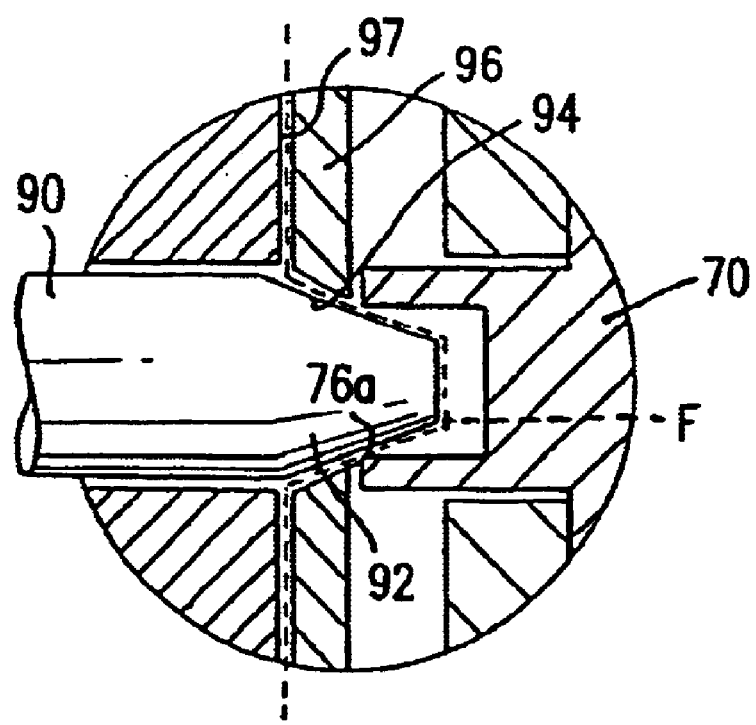
FIG. 12 is an enlarged cross-sectional view, partly in elevation, illustrating an alternative embodiment of the punch and anvil apparatus of the present invention, wherein a single punch member forms a hollow frusto-conical protrusion in the surface of the cover member for a dispenser package and the anvil member compresses the wall of the tip to form a peripherally extending fault line on the surface of the protruding tip.

In an alternate embodiment illustrated in FIGS. 12 and 13, a single punch 90 with a truncated end 92 can be used. The single punch 90 includes a bevelled surface 94 which engages the film or web F of thermoplastic material to form the generally frusto-conical hollow tip protrusion 34. As here embodied, thermoplastic web F is first clamped between shoulder plate 96 and face 97 of an outer punch member similar to punch 62. Thereafter, punch 90 advances, whereupon end 94 forms web F into frusto-conical tip 34, as shown as FIG. 13. As alternatively embodied, however, as best seen in FIG. 12, upon completion of the formation of tip 34, the peripheral edge 76a of anvil member 70 engages and compresses the outer surface of the frusto-conical wall of tip 34 to create a peripherally extending fault line 100a along the projecting surface of tip 34 between its base and apex.

Figure 12B:
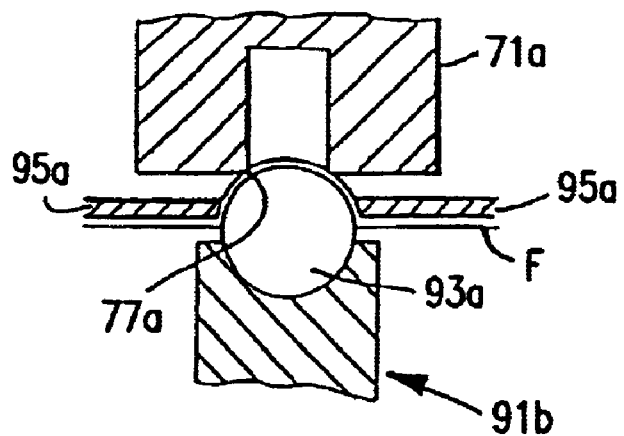
FIG. 12b is an enlarged cross-sectional view, partly in elevation, illustrating an alternative embodiment of the punch and anvil apparatus of the present invention, wherein a single punch member having a spherical tip forms a hollow mound protrusion in the surface of the cover member for a dispenser package and the anvil member compresses the wall of the tip to form a peripherally extending fault line on the surface of the mound.
Figure 13A:
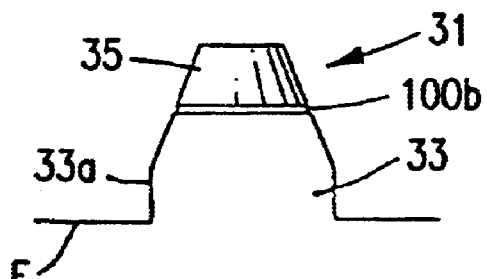
Figure 12A:
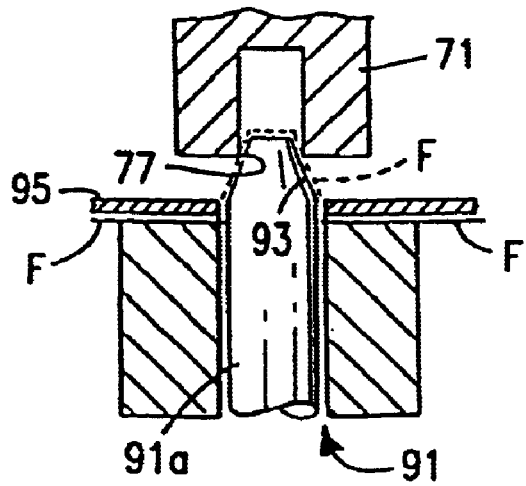
FIG. 12a is an enlarged cross-sectional view, partly in elevation, illustrating an alternative embodiment of the punch and anvil apparatus of the present invention, wherein a single punch member forms a hollow frusto-conical protrusion having a right-cylindrical base in the surface of the cover member for a dispenser package and the anvil member compresses the wall of the tip to form a peripherally extending fault line on the surface of the protruding tip.

In yet another alternative embodiment illustrated in FIGS. 12a and 13a, a single punch 91 with a beveled, truncated end 93 can be used to form the generally frusto-conical hollow tip protrusion 31. The single punch 91 engages the film or web F of thermoplastic material with the beveled surface 93.

Figure 14:
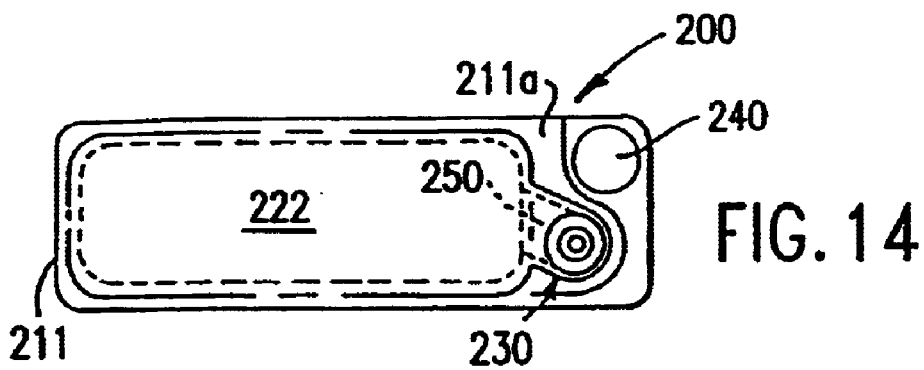
FIG. 14 is a top plan view of another embodiment of a dispenser package constructed in accordance with the present invention, wherein the breakaway tip and cap member are formed in a lateral extension of the cover member and the breakaway tip member communicates with the containment pouch through a shallow channel member.
Figure 15:
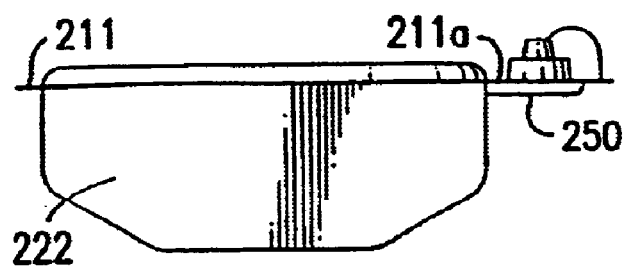
FIG. 15 is a side view of the embodiment illustrated in FIG. 14.
Figure 16:
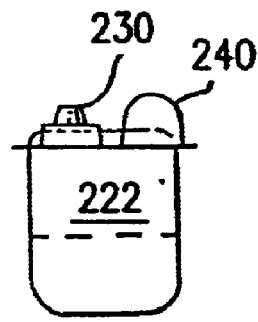
FIG. 16 is an end view of the embodiment illustrated in FIG. 14.

As with the embodiment shown in FIGS. 13 and 14, the thermoplastic web F is first clamped between stop plate 95 and clamp means 98 of an outer punch member. Thereafter, punch 91 advances, whereupon end 93 forms web F into the frusto-conical tip 31. As best shown in FIG. 13a, contact of the peripheral edge 77 of angle member 71 compresses the outer surface of the frusto-conical tip 31 to create a peripherally extending fault line 100b. In contrast to the embodiment shown in FIGS. 12 and 13, the stop plate 95 is situated adjacent the shaft of the punch 91, below the beveled, truncated end 93. Consequently, the thermoplastic web F is formed around the beveled end 93 as well as the right cylindrical shaft 91a. As can best be seen in FIG. 13a, the resulting frusto-conical tip 31 has a breakaway tip 35, a permanent projection 33, and a bright cylindrical section 33a. The right cylindrical section 33a is provided so a cap may be securely engaged with the tip 31.

In an alternative embodiment illustrated in FIG. 12b, a single punch 91B has a spherical tip 93A. The spherical tip 93A engages the thermoplastic web F to form a hollow mound protrusion. As embodied, the thermoplastic web F is first clamp beneath a stop plate 95A. Thereafter, punch 91B advances, whereupon the spherical end 93A forms web F into a hollow mound. Furthermore, the punch 91B is advanced forwards anvil 71A until the outer surface of the web F engages the peripheral edge 77A of anvil member 71A, thereby creating a fault line that extends around the tip of the mound structures. It has been found that the spherical tip 93A allows for self alignment of the punch 91B as the web F engages the peripheral edge 77A of the anvil 71A.

Figure 17:
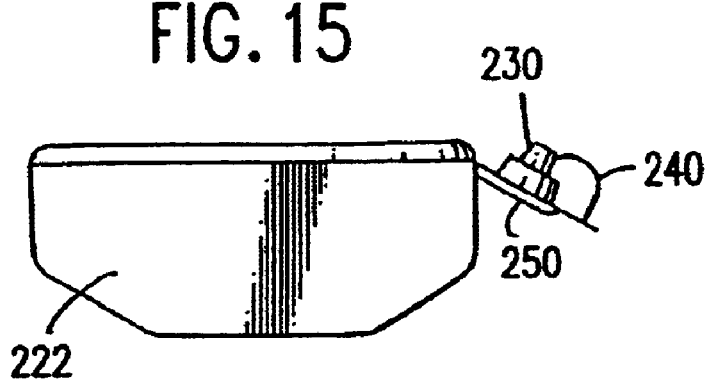
FIG. 17 is a side view of the embodiment of the invention illustrated in FIG. 14, wherein the lateral extension of the cover member also extends angularly downwardly.

Referring now more particularly to FIGS. 15–18 of the accompanying drawings, there is illustrated an alternate embodiment of the dispenser package of the present invention, indicated generally by reference manual 200. As here embodied, cover 211 includes a lateral extension 211a which extends beyond one end of the container pouch 222 and both the aperture-forming structure 230 and reclosure cap member 240 are formed in cover extension 211a. A shallow channel member 250 communicates aperture-forming structure 230 with the contents of pouch 222. Further alternatively, as shown in FIG. 17, lateral extension 211a of cover 211 is formed on an angle with respect to cover 11 so as to slope toward the pouch side of cover 11.

It has been found that the embodiments of FIG. 14–17 are advantageous in that they facilitate dispensing the contents of the package onto a surface, such as butter or cream cheese onto a slice of bread or toothpaste onto a toothbrush.

Figure 18:
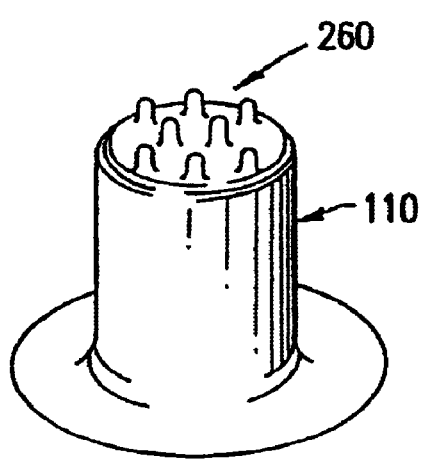
FIG. 18 is a schematic view of an alternate embodiment of the cap member, formed with bristles or nubs on its outer surface.
Figure 19:
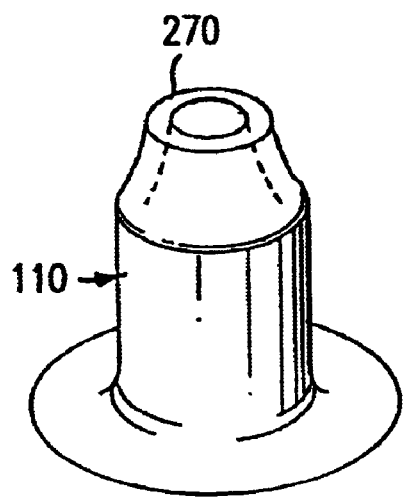
FIG. 19 is a schematic view of another alternate embodiment of the cap member, formed with a flattened spreader tool utensil on its outer surface.
Figures 20A, 20B, 20C, 20D:
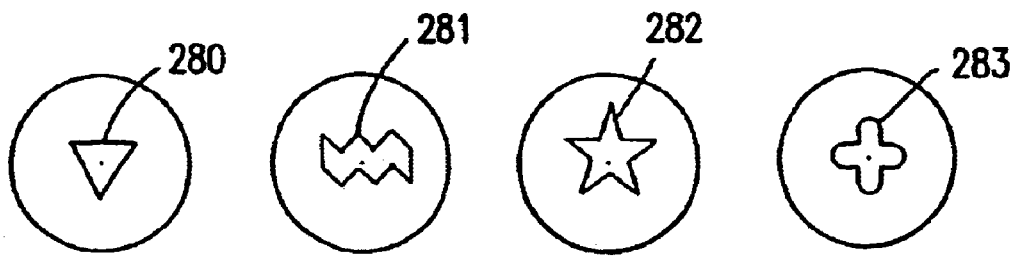
FIGS. 20a–d are partial end views of still other alternate embodiments of the cap member of the present invention, each view illustrating an open-ended cap member.
Figure 21A:
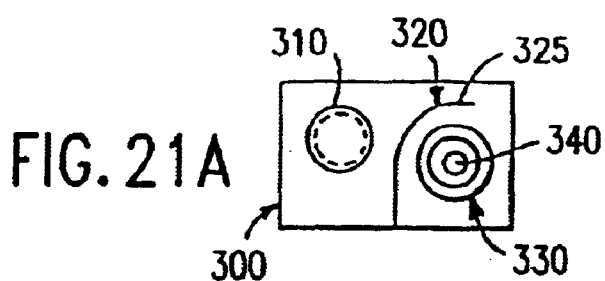
FIG. 21a is a top plan view of a reclosable outlet aperture forming structure which can be applied to various forms of containers in accordance with an alternate embodiment of the present invention.
Figure 21B:
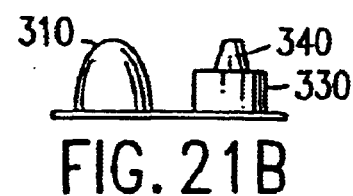

Referring now more particularly to FIGS. 18–20, there are shown several other alternative embodiments of the cap member of the present invention. Thus, as shown at FIG. 18, the top of resealing cap 110 may include bristles or nubs to function as a brush member; as shown in FIG. 19, the top of cap 110 may have a flattened surface 270 capable of functioning as a spreading tool; as shown in FIGS. 20a–d, cap 110 may be open-ended and have a shaped edge configuration, such as shown at 280, 281, 282, 283, respectively, so that the contents of the package may be expelled in a shaped stream.

With reference to FIGS. 21a–b and 22a–c, an alternate embodiment of the present invention will now be shown and described. In accordance with this alternate embodiment, an independent thermoforned unit is used to create an outlet aperture in a container. The independent thermoformed unit may take the form of a reclosable outlet forming structure 300. The reclosable outlet forming structure 300 may generally comprise a cap 310, a tether 320, a base 330, and a breakaway outlet tip 340. Cap 310 may be connected to base 330 via tether 320. Score 325 facilitates separation of the cap 310 from structure 300. The reclosable outlet forming structure 300 may have a pre-applied adhesive or sealant in the area surrounding the base 330 to facilitate application of the structure 300 to a container, such as milk container 302. As such, the structure 300 may be sealably or adhesively attached to any surface of a container requiring the subject outlet. In particular, the structure 300 may be sealed or adhered to the container in an area surrounding a hole in the container, but not in the area of the cap 310 or tether 320 which must be free of the container's surface. It is to be understood that reclosable outlet forming structure 300 may be attached to containers, such as milk carton 302, prior to filling. As such, the structure 302 may be applied to a container when it is still a flat blank.

Figure 22A:
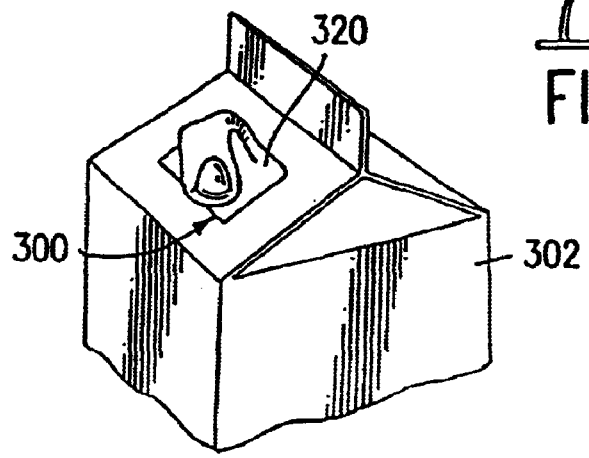
FIG. 22a is a perspective view of the reclosable outlet aperture forming structure of FIGS. 21a–b, as applied to a milk carton, in which the cap is placed over the outlet.
Figure 22B:
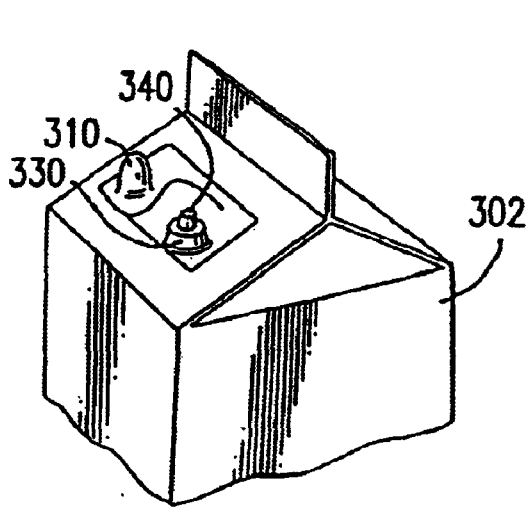
FIG. 22b is a perspective view of the reclosable outlet aperture forming structure of FIGS. 21a–b, as applied to a milk carton, in which the cap is removed from the outlet so as to allow removal of the breakaway outlet tip.
Figure 22C:
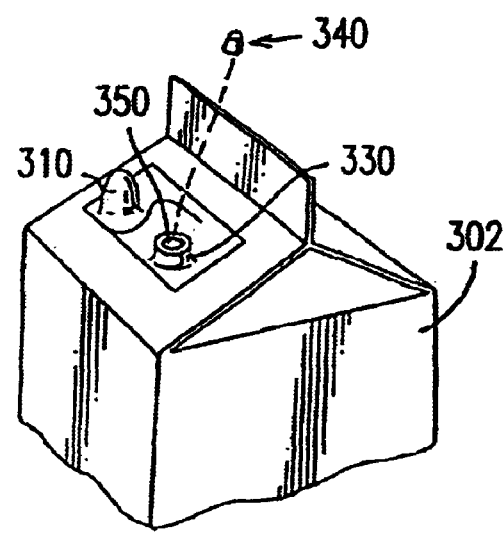
FIG. 22c is a perspective view of the reclosable outlet aperture forming structure of FIGS. 21a–b, as applied to a milk carton, in which the breakaway tip is removed from the outlet to form an opening therethrough.

With reference to FIGS. 22a–d, use of the reclosable outlet forming structure 300 will now be shown and described. With reference to FIG. 22a, prior to shipping of the container 302, the cap 310 may be placed over the outlet forming structure base 330 prior to removal of the breakaway tip 340 so as to assure that the breakaway tip 340 does not accidentally break and the contents of container 302 do not escape while the container 302 is in transit. With reference to FIG. 23b, the cap 310 is removed from base 330 to provide access to breakaway tip 340. The container at this point is ready for opening. With reference to FIG. 23c, the breakaway tip 340 is then removed to create an opening 350. Opening 350 leads to a hole (not shown) in container 302 to allow pouring the contents of container 302 therethrough. With reference to FIG. 23a, the reclosable outlet forming structure 300 may be resealed by simply placing the cap 310 over base 330.

In one embodiment of the present invention, base 330 and tip 340 are cylindrical or substantially cylindrical, although it is to be understood that other shapes may be used. In this embodiment, the opening 350 is made of PET-PVC-BAREX. It is to be understood, however, that other materials in accordance with the present invention may be used.

Figure 22D:
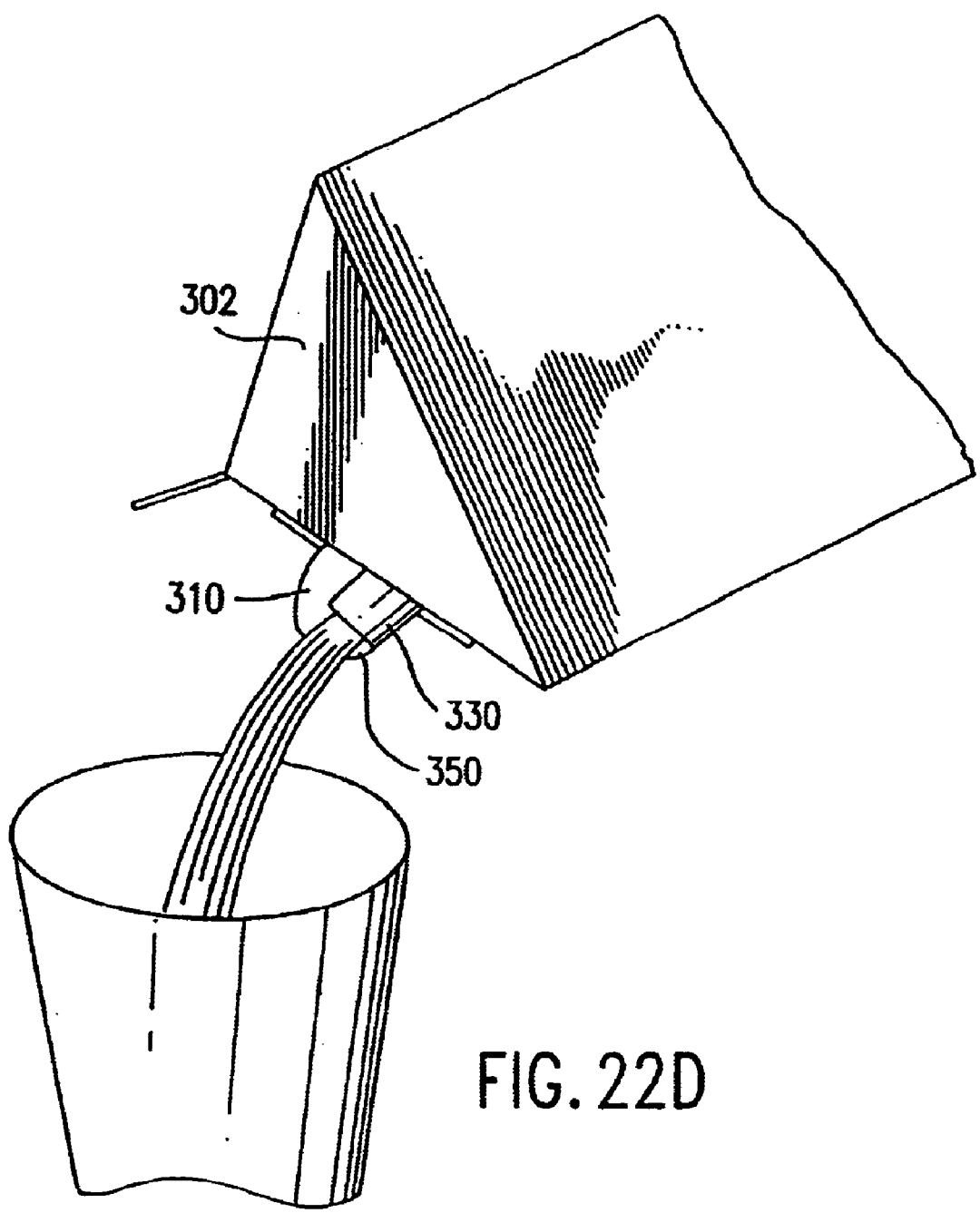
FIG. 22d is a perspective view of the milk carton of FIGS. 22a–c, in which the breakaway tip is removed from the outlet to form an opening through which milk is being poured.

As can be seen in FIG. 22d, the cylindrical outlet 330 and opening 350 act a nozzle direct the flow of the contents of the container 302 into a control stream.

Figure 23:
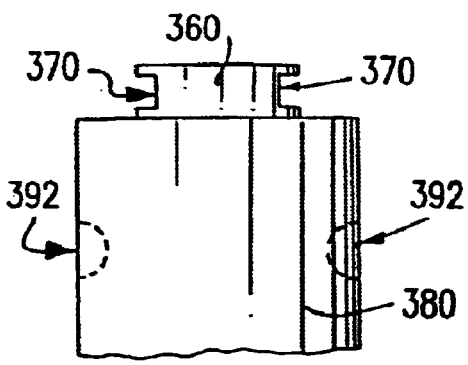
FIG. 23 is a side view of a low profile breakaway tip in accordance with another embodiment of the present invention.
Figure 24:
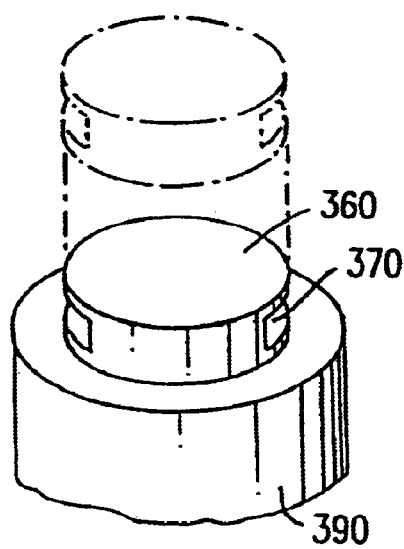
FIG. 24 is a top view of the low profile breakaway tip of FIG. 23.
Figure 23A:
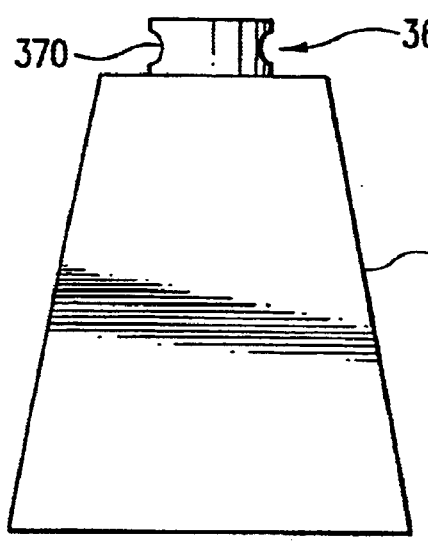
FIG. 23a is a side view of a low profile breakaway tip in accordance with another embodiment of the present invention.
Figure 25:
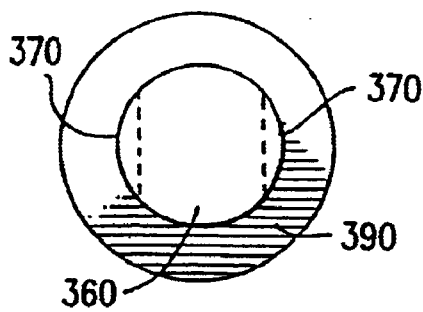
FIG. 25 is a perspective view of the low profile breakaway tip of FIG. 23 with the removed breakaway tip shown in phantom.
Figure 26:
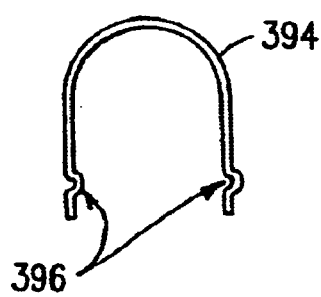
FIG. 26 is a side view of a cap for use with the low profile breakaway tip of FIG. 23.
Figure 27:
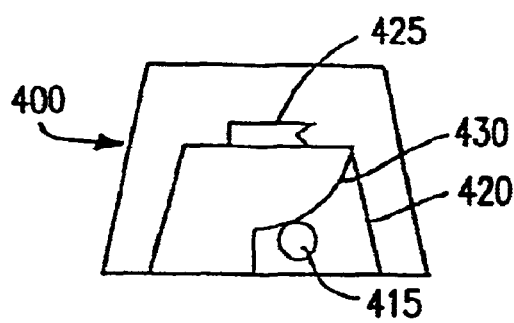
FIG. 27 is a side view of a another embodiment of the present invention which utilizes a twist-lock or twist-threading arrangement to secure the cap to the base formation.

With reference to FIGS. 23–26, a low profile breakaway tip and cap in accordance with another embodiment of the present invention is shown. In general, lowering the height of a breakaway tip 360 will lower the possibility that the tip 360 may be accidentally opened during transit or by handling. Lowering the height of the breakaway tip makes it more difficult, however, to grasp and remove the breakaway tip. This difficulty is alleviated by creating undercuts or indents 370 in the sidewall of the breakaway tip 360. These undercuts or indents 370 allows a user's finger to hook and break away the tip 360 in a single motion. FIG. 25 is a perspective view of the low profile breakaway tip with the removed breakaway tip shown in phantom. With continuing reference to FIGS. 23–25, the undercuts or indents 370 are preferably arranged in opposed positions to facilitate ease of use and manufacture. It is to be understood that the number and location of the undercuts/indents 370 may be varied. Once the breakaway tip 360 is removed from base 380, a cap 394 may be used to reclose the opening (not shown) exposed by the removal of tip 360 in base 390. Base indents 392 in base 380 are shaped and dimensioned to receive opposed inward protrusions 396 of cap 394. These protrusions 394 snap into indents 392, thereby securing cap 390 to base 380. A tether (not shown) may also be used to attach cap 390 to base 380.

Figure 24A:
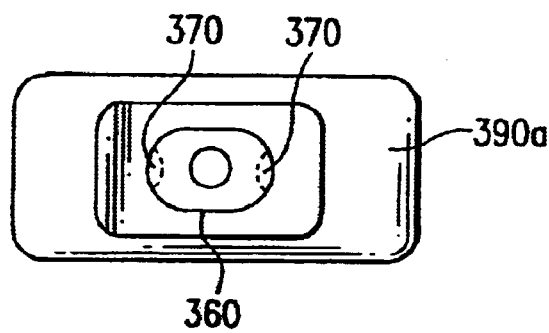

As shown in FIGS. 23a and 24a, the base 390a may have generally triangular cross-sectional area. Such a cross-sectional area, may aid in the dispensing of various materials. Furthermore, the relatively large bottom of the base 390a helps avoid accidental toppling of a container.

It is also to be understood that this embodiment of the present invention may be used in a wide variety of applications, including dispensers for creamers, unit dose medications, salad dressings, beauty aids, dental products, condiments, candy confections, syrups, granular products, etc. It is also to be understood that this embodiment of the present invention may be manufactured by utilizing a male punch member in conjunction with a self-centering and receding female anvil system, as previously shown and described.

Although the use of a tether limits the rotation of a cap pressed onto a base formation, a twist-lock or twist-threading arrangement may also be used to secure the cap to the base. With reference to FIG. 28, such an embodiment of the present invention which utilizes a twist-lock or twist-threading arrangement 400 to secure the cap 410 to the base formation 420 is shown. In this arrangement, cap 410 has an inner protrusion 415 which engages cam surface 430 of base 420. Upon rotation of cap 410 with respect to base 420, inner protrusion 415 engages cam surface 430 to create a twist-lock or twist-thread arrangement. It is to be understood that a tether (not shown) may also be used in such an arrangement. Base 420 may also have a breakaway tip 425 attached thereto.

Figure 28A:
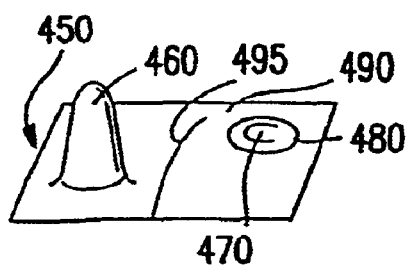
FIG. 28a is a perspective view of another embodiment of the present invention in which a tethered plug is used to open and close a pre-scored surface.
Figure 28B:
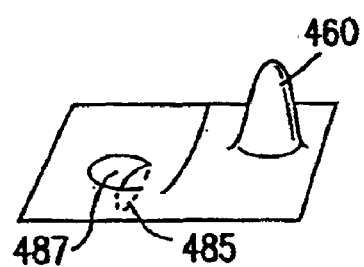
FIG. 28b is a perspective view of the embodiment of FIG. 29a in which the pre-scored surface has been opened.
Figure 28C:
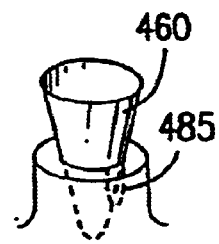
FIG. 28c is a perspective view of the embodiment of FIG. 28a in which the plug has been placed in the outlet hole, thereby opening the hole along the pre-scored surface and/or plugging the hole.
Figure 29A:
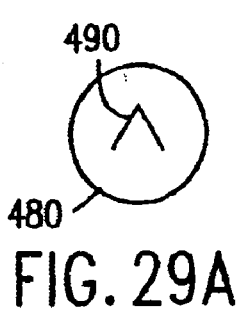
FIGS. 29a–d are top views of the outlet of the embodiment of FIG. 28a depicting various types of scored surfaces formed in the outlet.
Figure 29B:
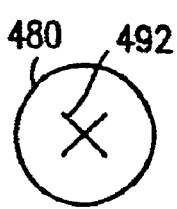
Figure 29C:
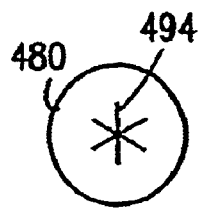
Figure 29D:
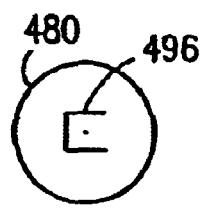
Figure 30A:
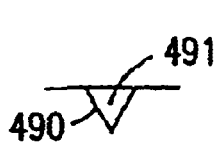
FIGS. 30a–d are side views of the scored surfaces shown in FIGS. 29a–d, in which each of the scored surfaces haves been penetrated to create an opening therethrough and a flap descending from the surface.
Figure 30B:
Figure 30C:
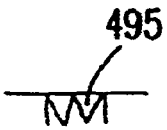
Figure 30D:
Figure 31:
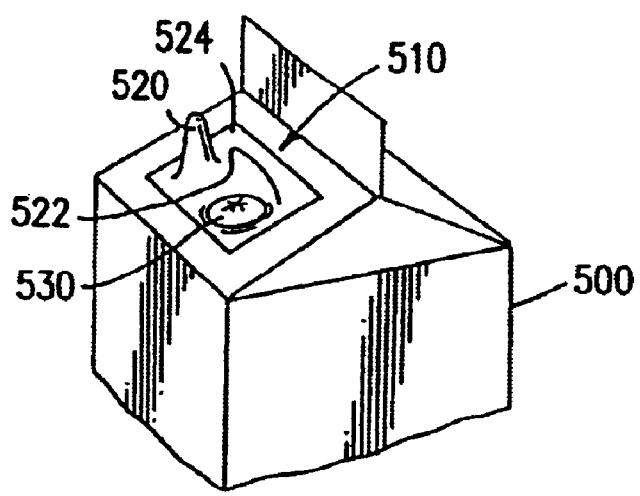
FIG. 31 is a partially elevated side view of an outlet forming structure according to an alternative embodiment of the present invention, having a punch/plug and a scored mount, as applied to a milk carton.
Figure 32:
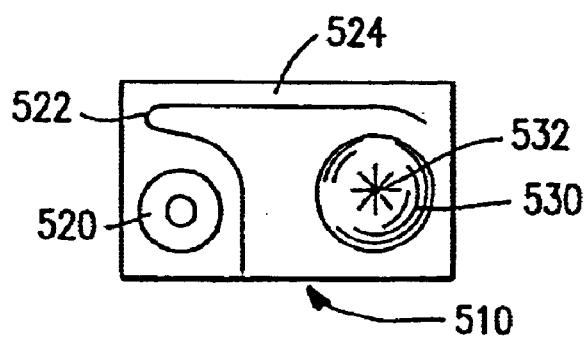
FIG. 32 is a top plan view of the outlet forming structure of FIG. 31.
Figure 33:
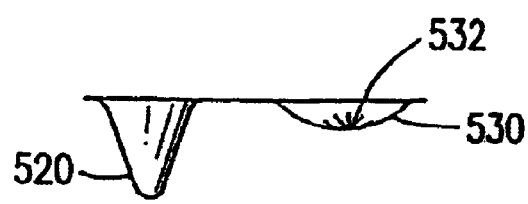
FIG. 33 is a side plan view of the outlet forming structure of FIGS. 31 and 32.

As an alternative to the breakaway tip and tethered cap arrangement, the present invention also includes a tethered plug/punch and scored surface arrangement as shown in FIGS. 28a–c, 29a–d and 30a–d. FIGS. 28a and 28b are perspective views of such an embodiment of the present invention in which a tethered plug is used to open and close a pre-scored surface. In this arrangement 450, a plug 460 is used to open a pre-scored surface 470 of outlet 480. In this embodiment, the score is in the form of an interrupted circle, although it is to be understood that other types of scored surfaces, such as those shown in FIGS. 29a–d, may also be used. FIGS. 28b and 28c depict a flap 485 which is created when plug 460 is used to penetrate the scored surface 470. A tether 490 may also be created through the use of a score 495 in arrangement 450. Plug 460, which may be connected to arrangement 450 via this tether 490, may also be used as a cork to close the outlet hole. As such, plug 460 may be used both as a plug and as an opening tool to create and/or plug an aperture in the pre-scored surface. In this embodiment, plug 460 has a conical shape, although it is to be understood that other shapes may be used. Similarly, as shown in FIGS. 28a and 29a–d, the score may have a partially circular shape, a V-shape, an X-shape, a star shape, or box shape, although it is to be understood that other patterns may also be utilized. Depending on the shape of the scored surface, the flap created by the penetration of plug 460 will differ. For example, the penetration of scored V-shaped surface 490 will create a flap 491; the penetration of scored X-shaped surface 492 will create a flap 493; the penetration of scored star-shaped surface 494 will create a flap 495; and the penetration of a scored surface 496 will create a rectangular-shaped flap 497.

An alternative embodiment of the present invention will now be discussed with reference to FIGS. 31–36. In accordance with this alternative embodiment, a container 500 is provided with a reclosable outlet forming structure 510. More specifically, the outlet former structure 510 comprises a curvilinear dome or mound 530 and a dual purpose punch/plug 520. As will be apparent to one of skill in the art, the container 500 includes a hole, not shown, over which the mound 530 is secured. Because the punch/plug 520 must be lifted and inverted for insertion into the scored area 532, it must not be sealed to the container 500. On the other hand, the mound 530 portion of the outlet forming structure 510 must be securely adhered over the hole in the container 500.

Figure 34:
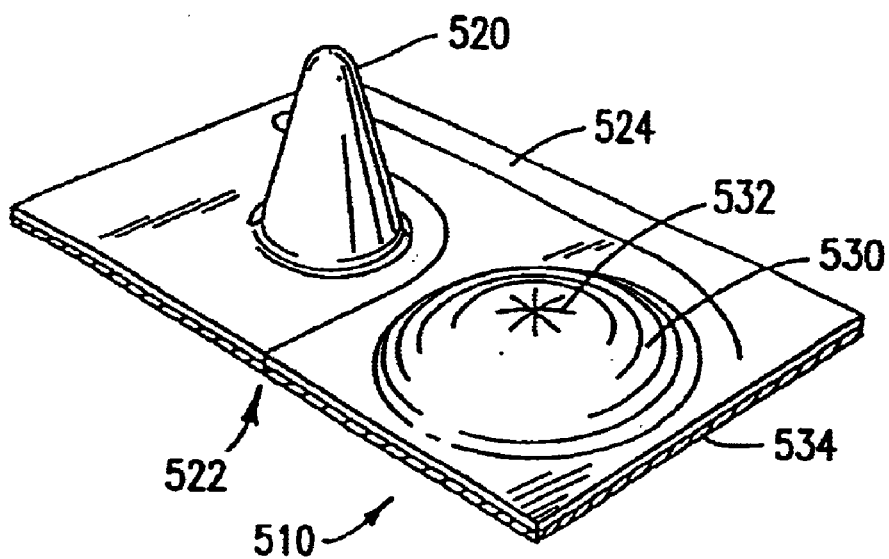
FIG. 34 is an enlarged elevated view of the outlet forming structure of FIGS. 31–33.

As can best be seen in FIG. 34, the outlet forming structure 510 comprises a layer of foil 534 laminated to the plastic forming the outlet forming structure 510. The portion of the foil 534 underneath the mound 530 should be unsupported other than the adhesive used to secure it to the mound 530. It should also be noted that the foil 534 is secured to the container 500, about the hole in the container 500, so that the contents do not leak out beneath the outlet forming structure 510. The foil laminated adhesive should be one that gives adequate adhesion but sets up with minimal tensile strength of its own. In alternative embodiments, the adhesive may approach being brittle.

Figure 35:
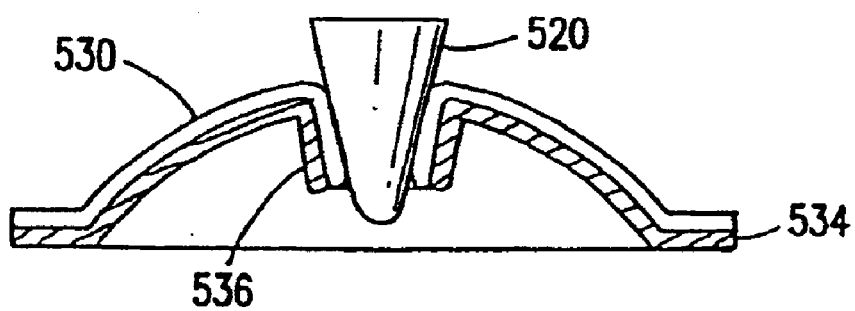
FIG. 35 is an enlarged side plan view of the outlet forming structure of FIGS. 31–34 showing the mound as punctured by the punch/plug.
Figure 36:
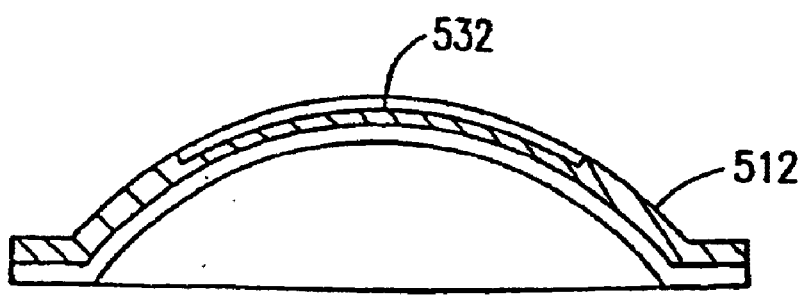
FIG. 36 is an enlarged side plan view of the mound of FIGS. 31–35.

The mound 530 further includes a fault line pattern or scored pattern 532. The fault lines 532 may take on any number of patterns, such as those shown in FIGS. 29*a–d*. As shown in FIGS. 35 and 36, the foil 534 is laminated to the entire surface of the mound 530 and preferably, is not scored. In an alternative embodiment, the adhesive may be omitted from the fault line pattern 532.

The punch/plug 520 is secured to the outlet forming structure 510 via a tether 524. The tether 524 is created by a cut 522 through the foil/plastic laminate. As can best be seen in FIG. 32, the cut 522 preferably takes a curvilinear path, following the periphery of the outlet forming structure 510. Such a cut 522 provides an elongated tether 524.

In operation, the punch/plug 520 is firmly pushed into the fault line pattern 532 to rupture the scored mound 530. This operation is best shown in FIG. 35. Having forced the punch/plug 520 through the scored area 532 of the mound 530, an opening for dispensing the contents of the container 500 is formed. The punch/plug 520 is removed from the mound 530 so that contents of the container 500 may be dispensed. Because the scored area 532 has been deformed to the shape of the punch/plug 520, the punch/plug 520 may be reinserted into the scored area 532, thereby resealing the container 500.

In an alternative embodiment, however, the foil layer 534 may span the hollow base of the mound 530 by being laminated only to the periphery of the mound. Of course, in such an embodiment, the punch/plug 520 must be long enough to extend past the plane of the foil 534 so that the foil 534 may be punctured. By wobbling the punch/plug 520 while inserted into the mound 530, the opening in the foil is enlarged.

It should be noted that the mound 530 strengthens the outlet forming structure 510. Furthermore, the shape of the mound 530 provides a nozzle finction, directing the contents of the container 500 in an even stream. Depending upon the contents of the container 500, the dimensions and shape of the mound 530 may be altered to provide the desired flow.

The outlet forming structure 510 of FIGS. 31–36 are preferably manufactured with a punch similar to that described with reference to FIG. 12*b*. Of course, the tip of the punch need not be spherical, but rather may be elliptical, parabolic, or any curvilinear shape. Furthermore, it is preferred that the foil and plastic be laminated into a single web prior to the formation of the mound be the punch. Thus, the dimensions of the mound, as defined by the shape of the punch tip, will be limited only be the physical properties of the materials used.

Figure 38:
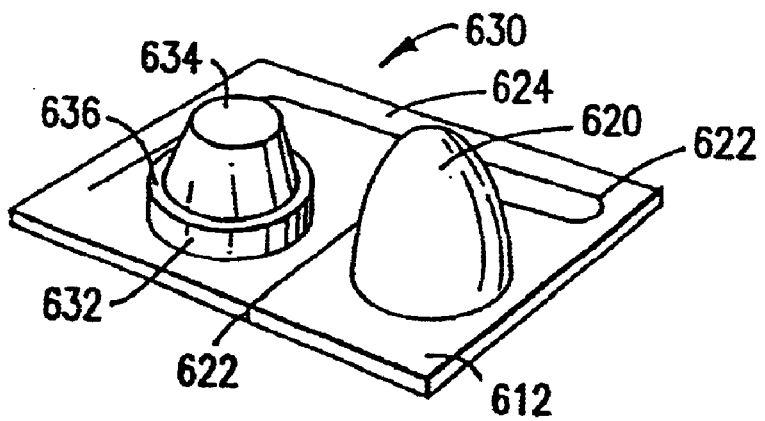
FIG. 38 is an enlarged side elevational view of the outlet forming structure of FIG. 37.
Figure 37:
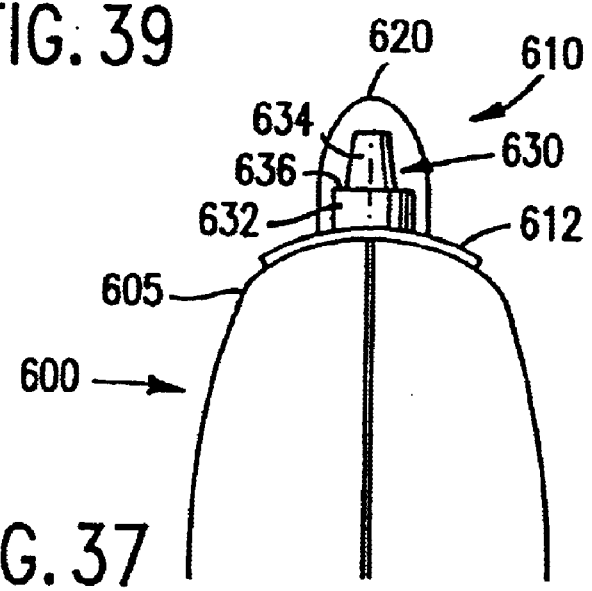
FIG. 37 is a side plan view of an alternative embodiment of the present invention in which an outlet forming structure, having a breakaway tip and cap, is applied to a foil package.

In an alternative embodiment, which will now be described with reference to FIGS. 37–38, a reclosable outlet forming structure 610 according to the present invention is utilized with a flexible plasti-foil pouch 600. In general, the foil pouch 600 is formed by folding a generally rectangular shaped piece of the foil plastic combination in half and sealing the three open edges thereof. A reclosable outlet forming structure 610 is mounted on the seamless end 605 of the pouch 600. The outlet forming structure 610, which is sealed to the seamless end of the pouch 600 by applying an adhesive around a periphery of the base 612, covers a hole, not shown, in the pouch 600.

The outlet forming structure 610 may be of any type previously disclosed above, such as those described with reference to FIGS. 1–3, 8–9, 13, and 13*a*. In a preferred embodiment, as shown in FIGS. 37 and 38, the outlet forming structure 610 includes an aperture forming protrusion 630. More specifically, the aperture forming protrusion 630 includes a hollow cylindrical base 632 and a break-away tip 634. A fault line 636 extends around the periphery of the protrusion structure 630, permitting the breakaway tips 634 to be broken away from the base 632 in the tip 634. More specifically, the fault line 636 is a narrowed, stress concentrating area.

The outlet forming structure 610 also includes a cap 620. The cap 620 is a hollow tapered member, which has an inside base diameter slightly larger than the outside diameter of the base 632 of the protrusion structure 630. The cap 620 is secured to the outlet forming structure 610 via a tether 624. The tether 624 is formed by a cut 622 through the lower surface 612 of the outlet forming structure 610. As can best be seen in FIG. 39, the curvilinear cut 622 separates the cap 620 from the protrusion structure 630 and follows the periphery of the base 612. By having such a pattern, the cut 622 is relatively long and, consequently, produces a relatively long tether 624. Due to the long tether 624 and the fact that the portion of the base 612 that supports the cap 620 is not fastened to the pouch 600, the cap 620 may be raised and securely placed over the outlet forming structure 630.

In operation, a user applies sidewise finger pressure to the protrusion tip 634, thereby causing it to break away from the protrusion base 632 along a fault line 636. Because the protrusion structure 630 is substantially hollow, an aperture, not shown, is created. Furthermore, because the protrusion member 630 has been affixed to the pouch 600 over a hole in the pouch, not shown, the contents of the pouch 600 may be dispensed via the now opened protrusion neck 632. The cap 620 is placed over the base 632 during shipping, so that accidental rupturing of the fault line 636 is prevented. Furthermore, cap 620 is placed over the base 632 to reclose the package 600 when only a portion of the contents of the package 600 has been dispensed.

Figure 39:
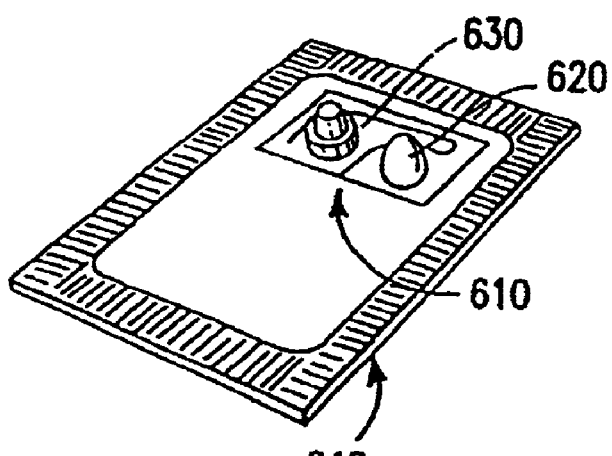
FIG. 39 is an elevated plan view of an alternative embodiment of the present invention as applied to a foil package.

In an alternative embodiment, shown in FIG. 39, the same outlet forming structure 610 is secured to the side of pouch 640. In this embodiment, the pouch 640 is formed from two generally rectangular sheets of foil plastic laminate which are sealed together around all four sides of each sheet. As with the previous embodiment, the protrusion structure 630 is affixed to the pouch 640 over a hole, not shown, so the protrusion neck 632 is in fluid communication with the contents of the pouch 640.

Figure 38A:
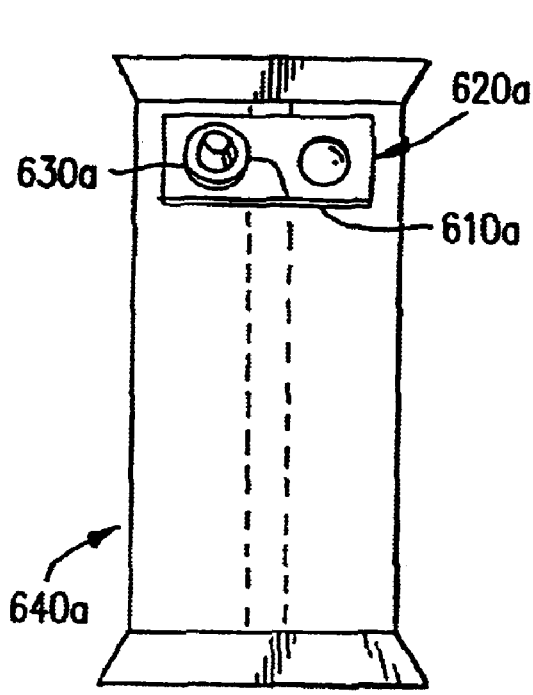
Figure 37A:
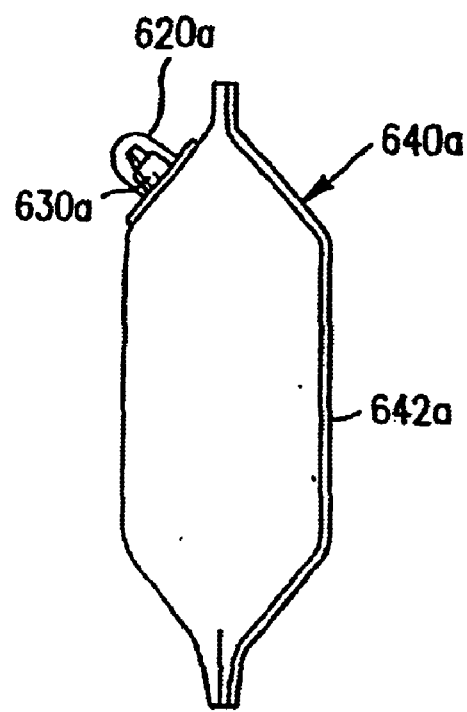
FIG. 37a is a side plan view of an alternative embodiment of the present invention in which an outlet forming structure is applied to a foil package.
Figure 39A:
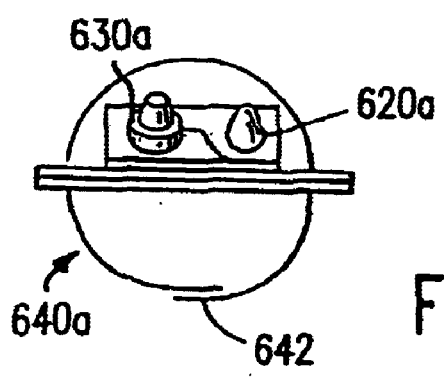

An alternative embodiment of the present invention employing an outlet forming structure 610*a* disposed on a foil pouch 640*a* will now be described with reference to FIGS. 37*a*, 38*a*, and 39*a*. Briefly described, the outlet forming structure 610*a* is substantial the same as the outlet forming structure described with reference to FIGS. 37–39. Specifically, the outlet forming structure 610a includes both a cap 620a and a protrusion member 630a. As best seen in FIG. 39a, the foil pouch 640a includes a lap seam on the side opposite the outlet forming structure 610a.

Figure 40:
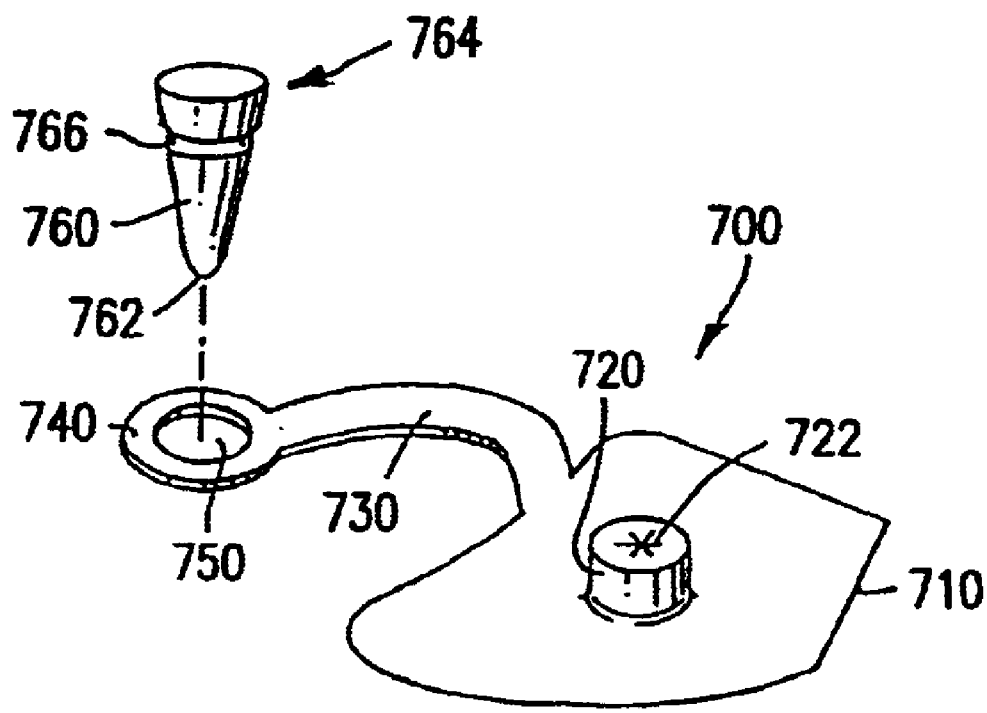
FIG. 40 is a partial elevational view of an outlet forming structure according to another alternative embodiment of the present invention, having a snap-in auxiliary punch/plug/cap and protrusion member, that is manufactured by a pick-and-place method.

An alternative embodiment of the present invention will now be described with reference to FIG. 40. A tethered punch/plug and base member with a star shaped fault pattern manufactured as a unit 700 is shown. A tether 730 is connected to the base 710 at a proximal end thereof, a ring structure 740 connected to a distal end thereof, and a tapered punch/plug 760. The punch/plug 760 is manufactured separately from the other components.

As shown, the ring structure 740 defines an opening 750. The opening 750 is larger than the tip 762 of the punch/plug 760 yet smaller than the base 764 of the punch/plug 760. Furthermore, the punch/plug 760 includes a circumferential indentation 766. The indentation 766 is formed on the punch/plug 760 just below a point where the outside diameter of the punch/plug 760 becomes larger than the inside diameter of the opening 750.

Therefore, once the components have been separately manufactured, the punch/plug 760 is snapped into the opening 750. When snapped into the opening 750, the tapered punch/plug 760 causes the slightly elastic ring structure 740 to expand until the ring structure 740 reaches the indentation 766. Upon reaching the indentation 766, the ring structure 740 snaps into the indentation 766. Consequently, the punch/plug 760 becomes connected to the ring structure 740 and the other components.

Figure 40A:
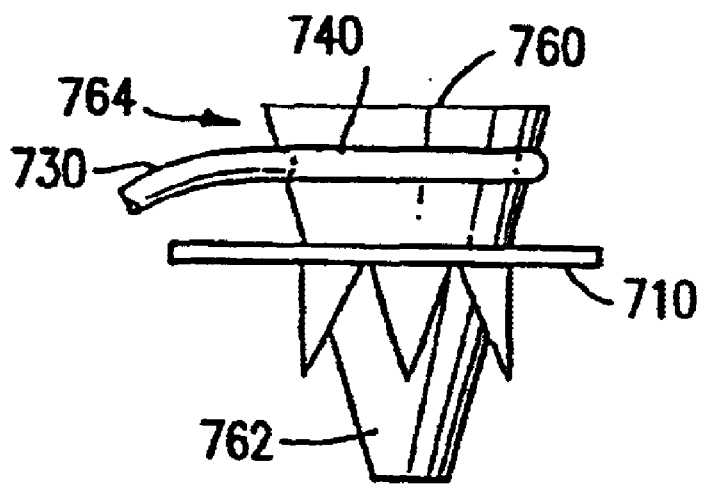
FIG. 40a is an enlarged side plan view of the outlet forming structure of FIG. 40 showing the punch/plug/cap puncturing the protrusion member.

In use, as shown in FIG. 40a, the punch/plug 760 is used to puncture the scored section 722 of the protrusion structure 720. Such operation is described in greater detail with reference to FIGS. 28–30d.

Figure 41:
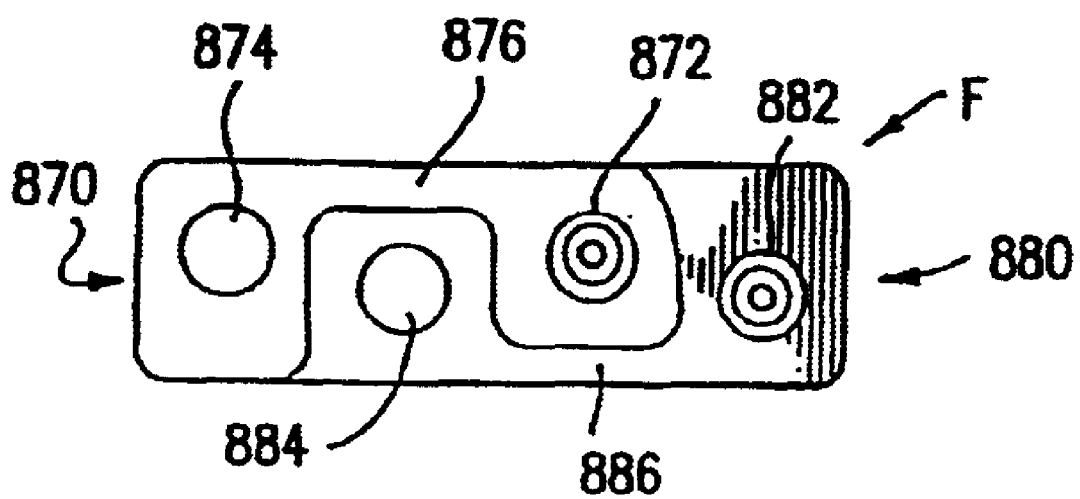
FIG. 41 is a top plan view of an alternative embodiment, wherein the outlet forming structures are formed from a single thermoplastic web in a mating arrangement.

Turning now to FIG. 41, one embodiment for manufacturing a reclosable outlet forming structure according to the present invention is shown. Specifically, a pair of reclosable outlet forming structures 870 and 880 are formed from the same piece of thermoplastic web F. Each reclosable outlet forming structure 870, 880 comprises a protrusion structure 872, 882 as well as cap 874, 884, respectively. As in the previously disclosed embodiments, each cap 874, 884 is connected to the corresponding protruding structure 870, 880 via a tether 876, 886.

It is to be understood that the mating, horse-shoe arrangement of the outlet forming structures 870, 880 provides several benefits, such as reclining wasted portions of the web F, and that the manufacturing agreement may be repeated along the length of the web F.

Figure 42:
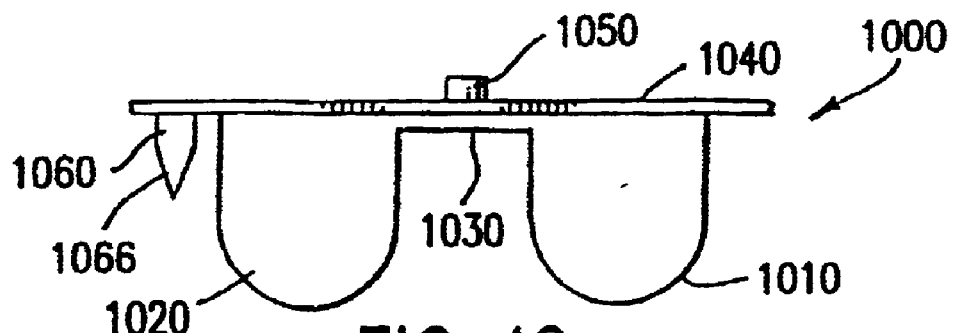
FIG. 42 is a side plan view of an alternative embodiment of the present invention in which the reclosable container is provided with a scored protrusion and a dual purpose tethered punch/cap.
Figure 43:
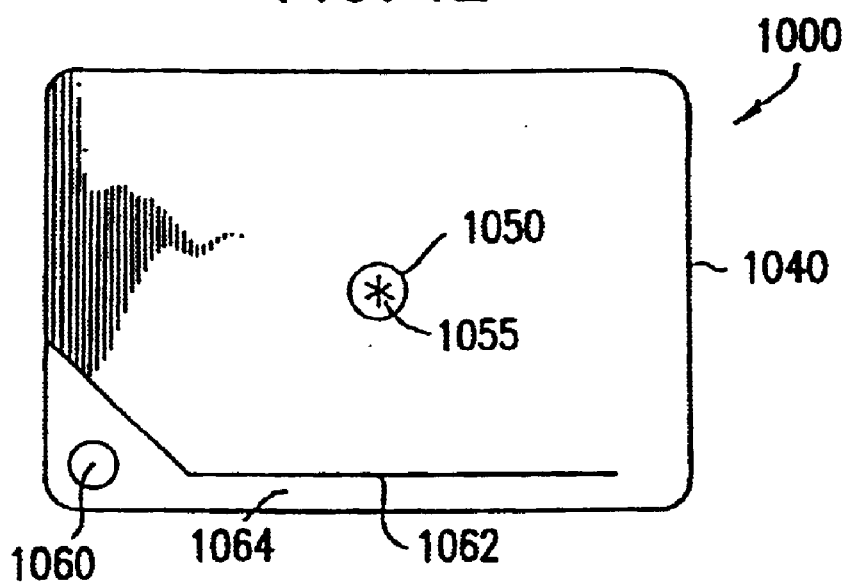
FIG. 43 is a top plan view of the reclosable container of FIG. 42.
Figure 44:
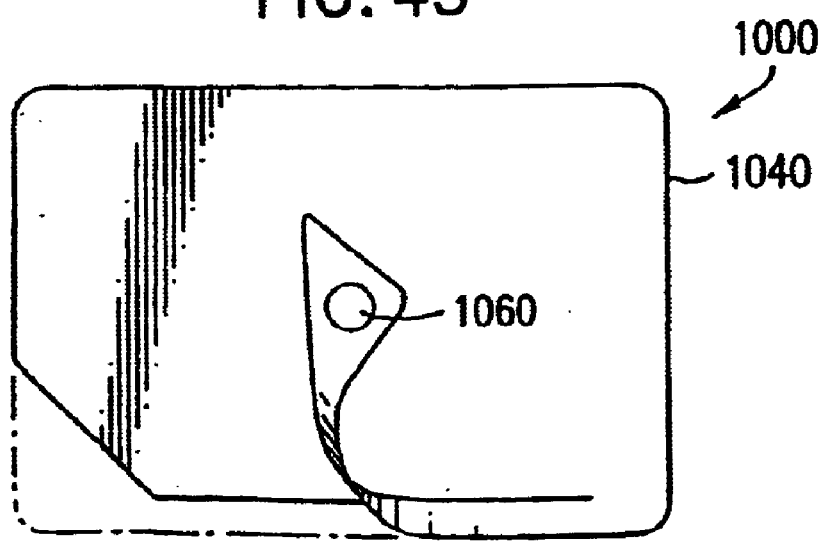
FIG. 44 is a top plan view of the reclosable container of FIGS. 42 and 43, wherein the tethered punch/cap is securely fastened over the scored protrusion.

Turning now to FIGS. 42–44, an alternative embodiment of the present invention is shown. Initially, it should be noted that the container 1000 shown is made of similar materials as described above with reference to FIG. 1–3.

The container 1000 comprises a first deformable pouch 1010 and a second deformable 1020. The two pouches 1010, 1020 are joined by a shallow conduit 1030. The deformable pouches 1010, 1020, as well as the joining conduit 1030, are sealed by a generally flat sheet 1040 of thermoformable plastic material. A hollow protrusion 1050 is integrally formed with the flat sheet of thermoformable plastic 1040. The hollow protrusion 1050 extends from the flat sheet 1040. The protrusion 1050 is directly above and in fluid communication with the conduit 1030. The container 1000 further includes a punch/cap 1060.

As can best be seen in FIG. 43, the hollow protrusion 1050 has scores or fault lines 1055 on the top face thereof. Despite these fault lines 1055, which weaken the protrusion 1050, the container 1000 remains sealed. Further shown in FIG. 46, the punch/cap 1060 is partially separated from the remainder of the container 1000 by cut 1062. The cut 1062 which parallels one peripheral edge of the container 1000 creates a tether 1064.

In order to open the container 1000, the punch/cap 1060 is positioned over the protrusion 1050. The punch/cap 1060, and more specifically the pointed end 1066 of the punch/cap 1060 is forced through the score or fault lines 1055, thereby opening the hollow protrusion 1050. When punch/cap 1060 is removed from the hollow protrusion 1050, an opening, not shown, exists. The opening is formed by the permanent deformation of the portion of the protrusion member 1050 between the fault lines 1055. By inverting the container 1000 and gently squeezing either or both of the pouches 1010, 1020 the material contained within the pouches is dispensed via the opening in the protrusion 1050.

It should be noted that in the preferred embodiment the protrusion 1050 is placed directly above the conduit 1030. As a result, the contents of the pouches 1010, 1020 can be dispensed in a controlled manner. Specifically, the shallow conduit 1030 provides resistance to the flowing contents so that the contents do not spout from the opened protrusion 1050 uncontrollably, particularly when the protrusion 1050 is initially punctured.

As shown in FIG. 44, should less than all of the material contained within the pouch 1010, 1020 be dispensed, the container 1000 may be reclosed. Specifically, the punch/cap 1060 is inverted by twisting the tether 1064. Because the punch/cap 1060 is hollow, having an inside diameter substantially the same as or slightly larger than the outside diameter of the protrusion 1050, the punch/cap 1060 can be securely placed on the protrusion 1050.

With regard to the embodiment of FIGS. 42–44, it will be apparent to one skilled in the art that the invention is not limited by the type of outlet forming structure utilized. Specifically, any combination of break away tip, scored protrusion member, punch, plug, and cap may be employed. Furthermore, it should be understood that the particular shape of the pouches may vary according to the properties of the contents held therein.

Figure 45:
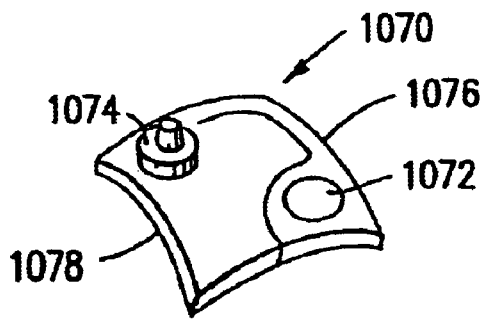
FIG. 45 is an elevated plan view of an outlet forming structure according to one embodiment of the present invention.
Figure 48:
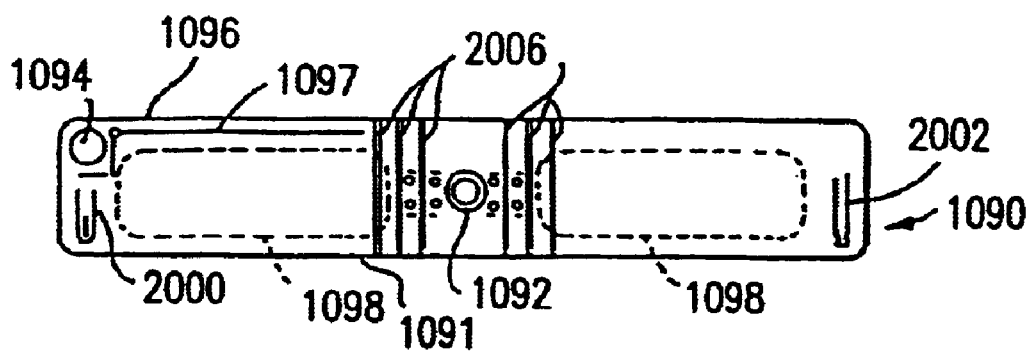
FIG. 48 is a top plan view of a container according to an embodiment of the present invention.
Figure 49:
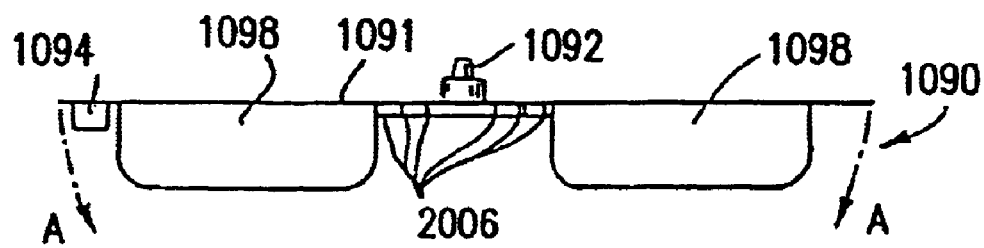
FIG. 49 is a side plan view of the container of FIG. 49.

An alternative embodiment of the present invention will now be described with reference to FIGS. 45–47. As shown in FIG. 45, an outlet forming structure 1070 comprises a cap member 1072 and an aperture forming protrusion 1074. As with the embodiments discussed above, the cap member 1072 is connected to the aperture forming structure 1074 by a tether 1076. As can be seen, both the cap member 1072 and the aperture forming structure 1074 are formed in a curvilinear base 1078.

Figure 46A:
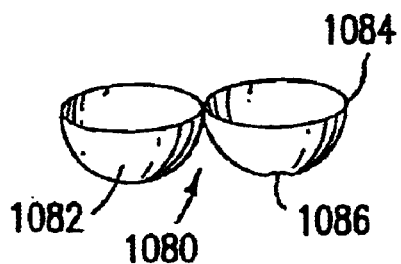
FIGS. 46a–c are side plan views of a container for use with an outlet forming structure according to the present invention.
Figure 46B:
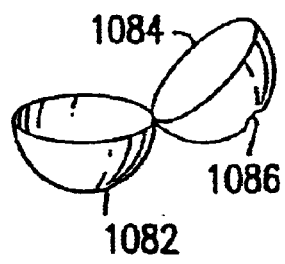
Figure 46C:
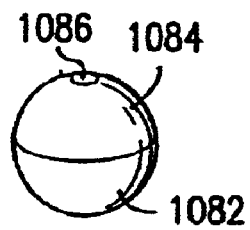

Because the outlet forming structure 1070 is formed in a curvilinear base 1078, it may be positioned on a container 1080 having a similar curvilinear surface. As shown in FIGS. 46a–c, one such container 1080 is generally spherical and formed in two halves 1082, 1084. The two halves 1082, 1084 are joined at one point along their circumferences, and are therefore hingeably connected. One half 1084 of the container 1080 includes an aperture 1086 formed therein.

Figure 47:
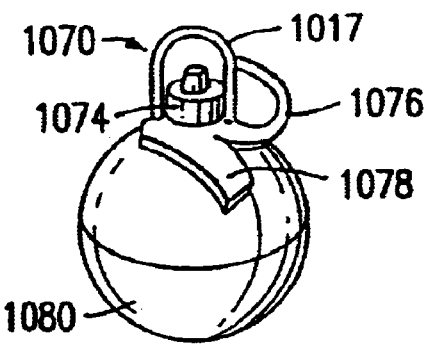
FIG. 47 is an elevated plan view of the container of FIGS. 46a–c with the outlet forming structure of FIG. 45 mounted thereon.

In operation, as shown in FIG. 47, the outlet forming structure 1070 is affixed to the container 1080 such that the aperture forming structure 1074 is in alignment with the aperture 1086 in the container 1080. As further depicted in FIG. 47, the cap member 1072, shown in a sectional view, may be positioned over the aperture forming structure 1074, thereby protecting it and sealing the container 180. It is to be understood that the shape of the container 1080 is merely representative of those that may be employed with the present invention, as the outlet forming structure may be formed on a curvilinear base having virtually any shape.

Another alternative embodiment of the present invention will now be described with reference to FIGS. 48–51. The container 1090 generally comprises a rectangular sheet 1091 of thermoformable material. At the center of the rectangular sheet 1091 is an aperture forming structure 1092, having a base and break away tip as described above with reference to the prior embodiments. On either side of the aperture forming structure 1092 are pouches 1098 formed on the underside of the sheet 1091 for holding any flowable substance. The pouches 1098 are in fluid communication with the aperture forming structure 1092.

Also formed in the rectangular sheet 1091 of thermoformable material is a cap member 1094. The cap member 1094 is preferably formed in one corner of the rectangular sheet 1091 and attached to the container 1090 via a tether 1096. The tether 1096 is formed by a cut 1097 extending along the perimeter of the container 1090.

The container 1090 may be folded generally in half along bending grooves 2006 disposed on either side of the aperture forming structure 1092. Specifically, the ends of the container 1090 are brought together as depicted by arrows "A" in FIG. 49. Once the ends are brought together, a female package tie 2000 and a male package tie 2002, both of which are integrally formed in the sheet of thermoformable material 1091, are brought into engagement.

Figures 50, 51:
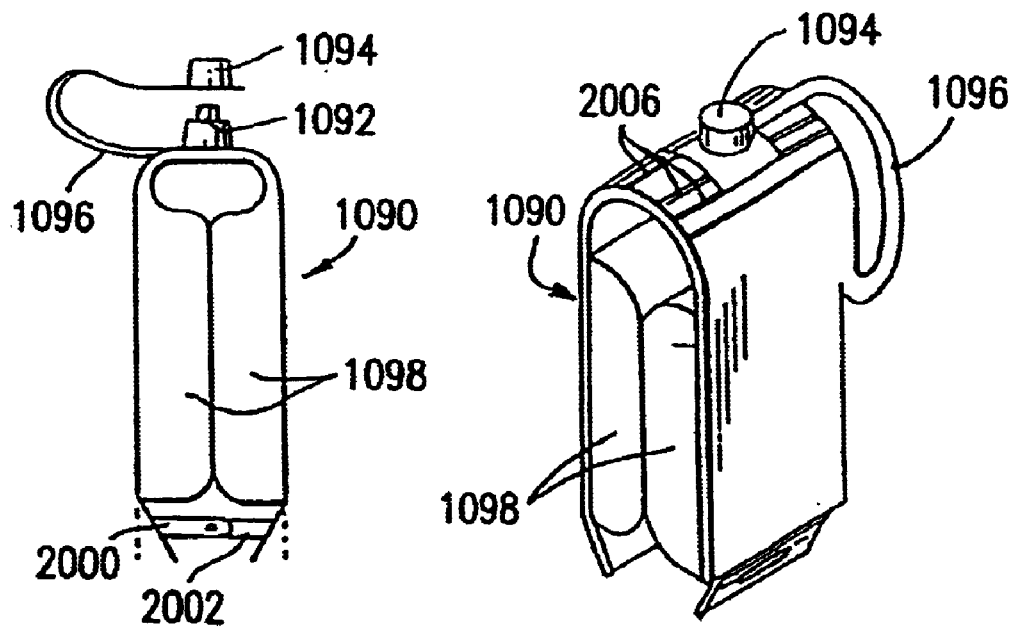
FIG. 50 is a side plan view of the container of FIGS. 48 and 49 in a closed position.
FIG. 51 is a side perspective view of the container of FIGS. 48–50.

Engagement of the female package tie 2000 and the male package tie 2002 hold the container 1090 in the configuration as shown in FIGS. 50 and 51. In operation, lateral finger pressure on the tip of the aperture forming structure 1092 causes a fault line to rupture, thereby forming an aperture in the aperture forming structure 1092. Thus, the contents of the container 1090 may be dispensed from the aperture. As shown in FIG. 51, the cap member 1094 may be placed over the aperture forming structure 1092, thereby preventing accidental rupturing of the fault line or accidental dispensing of the contents after the tip of the aperture forming structure 1092 has been removed.

Figure 54:
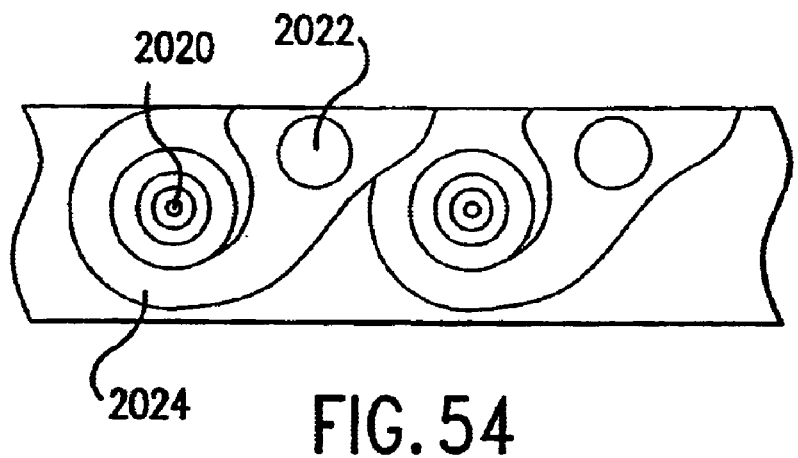
FIG. 54 is a top plan view of a section of a web of thermoformable material having a series of outlet forming structures formed therein.
Figure 53:
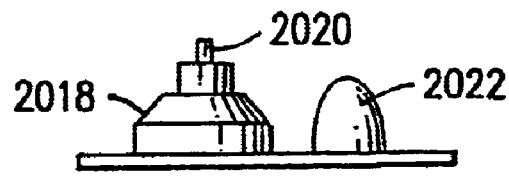
FIG. 53 is an enlarged side plan view of the outlet forming structure of FIG. 52.
Figure 52:
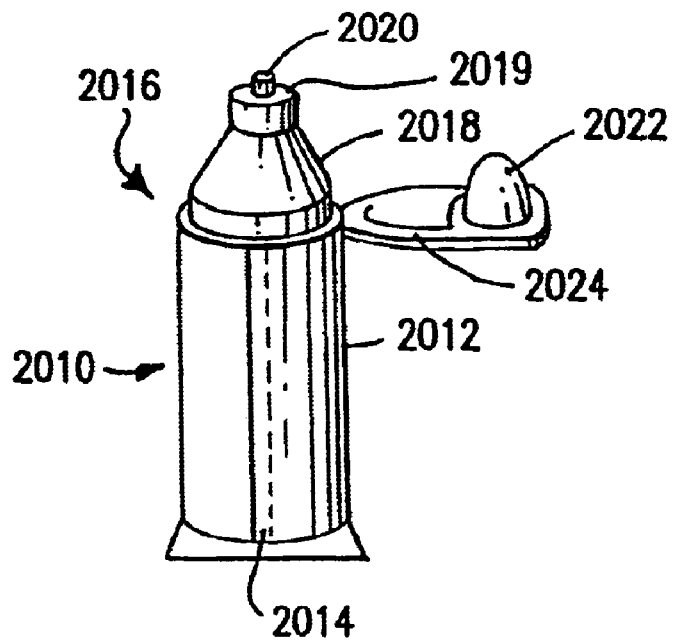
FIG. 52 is a side elevational view of a container according to an embodiment of the present invention.
Figure 55A:
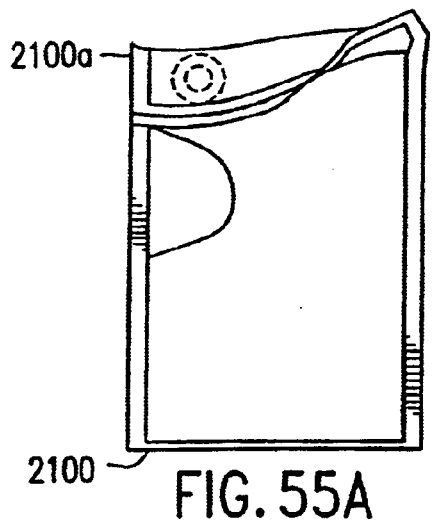
FIGS. 55a–55f disclose various views of a sachet with a breakaway tip formation.
Figure 55B:
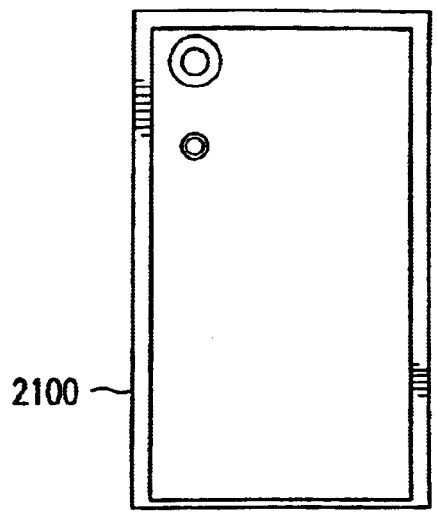
Figures 55C, 55F:
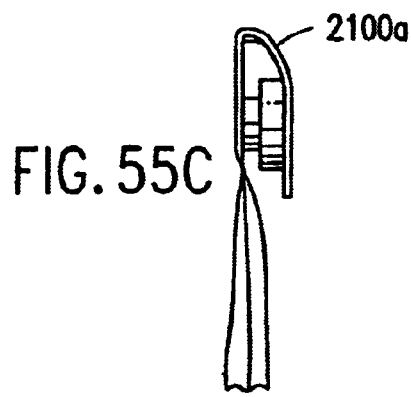
Figure 55D:
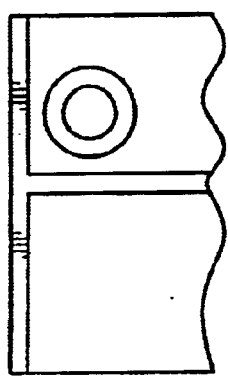
Figure 55E:
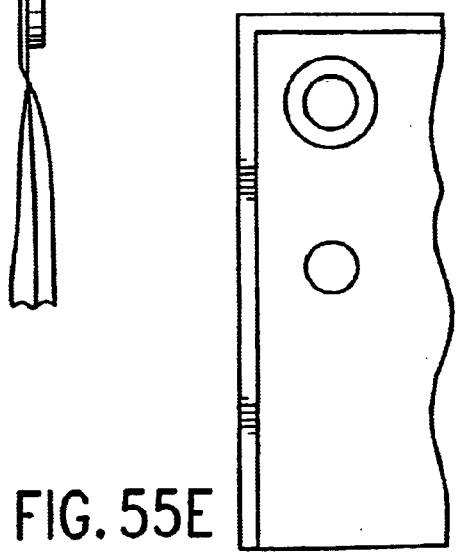
Figure 57A:
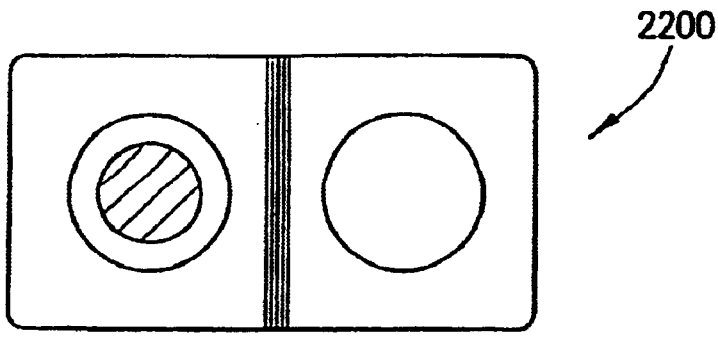
FIGS. 57a–57d disclose various views of a reclosable aperture forming means with a breakaway tip remaining attached to the cap after opening.
Figure 57B:
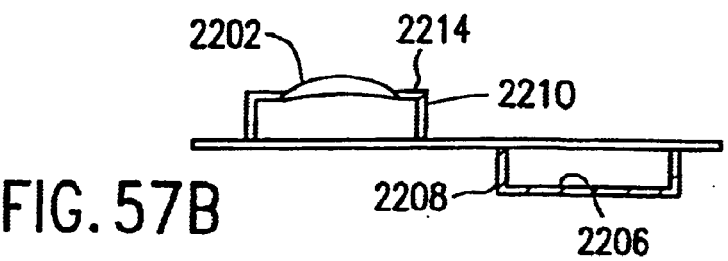
Figure 57C:
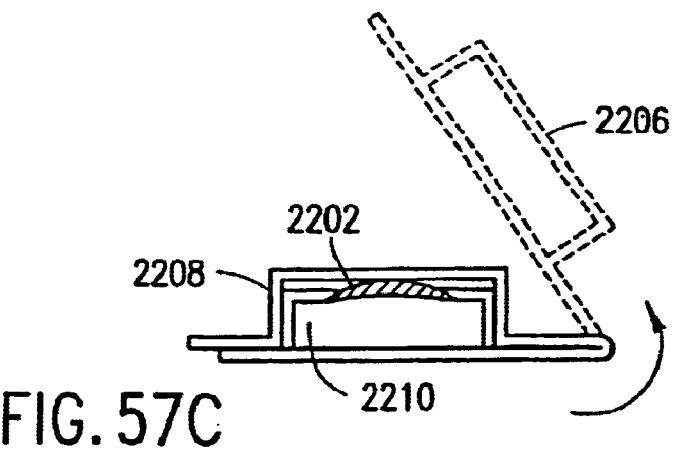
Figure 57D:
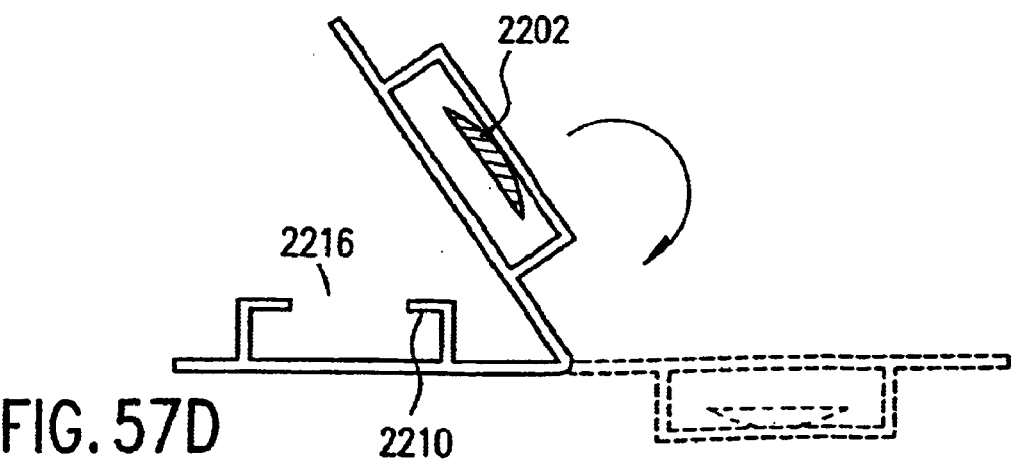
Figure 58A:
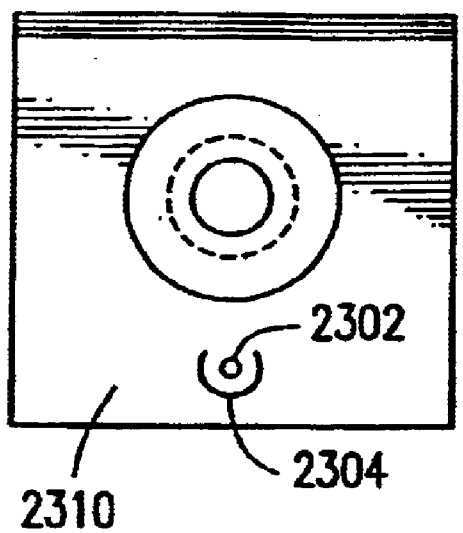
FIGS. 58a–58b disclose a further tampering evidence and a grip hole.
Figure 58B:
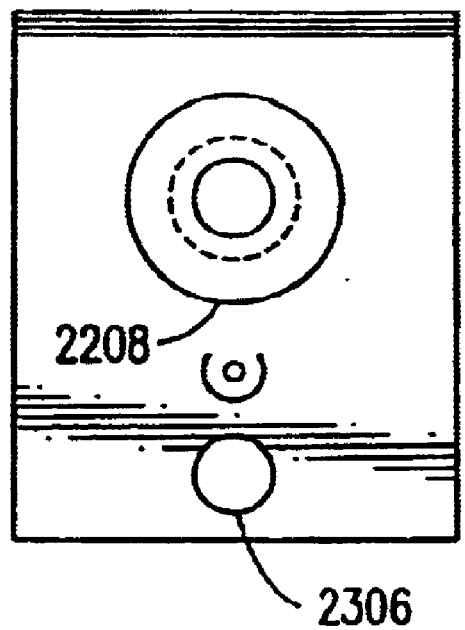

Another alternative embodiment of the present invention will now be described with reference to FIGS. 52–54. As shown in FIG. 52, an aperture forming structure 2016 according to the present invention may be positioned on a treated paper board tube 2012, thereby forming a sealed container 2010. The aperture forming structure 2016 comprises a generally hollow frusto-conical portion 2018, a hollow cylindrical portion 2019, and a breakaway tip 2020. Integrally formed with the aperture forming structure 2016 is a cap member 2022 and an associated tether 2024. As can best be seen in FIG. 54, the tether 2024 is formed by a curvilinear cut which allows the cap member 2022 to be partially separated from the aperture forming structure 2016 so that the cap member 2022 may be positioned over the cylindrical portion 2019 and the breakaway tip 2020. Because the cap member 2022 has an inside diameter slightly larger than the outside diameter of the cylindrical portion 2019, the cap member 2022 fits snugly thereon, thereby sealing the container 2010.

As with the previously described embodiments, in operation, lateral pressure on the breakaway tip 2020 causes it to separate from the rest of the aperture forming structure 2016, thereby forming an aperture into the generally hollow aperture forming structure 2016. Thus, the contents of the container 2010 may be dispensed therefrom.

Another alternative embodiment is described in FIGS. 55a through 56c. This embodiment relates to a pouch or sachet like container 2100 generally used for dispensing such products as ketchup, condiments, salad dressing and many non-food products such as surgical jelly, etc. Many pouches have a serious flaw in that they are difficult to open and messy. This embodiment relates to a sachet 2100 which is simple to open and cleanly dispenses product.

As shown in FIGS. 55a–56c, the sachet 2100 has a breakaway tip formation formed into the wall or face of the sachet located near one of its corners. By bending the end having the tip 2100c on it over and sealing the tip to the same wallface of the sachet 2100 the tip is then located to form a system which is easily and neatly opened. The user simply grasps the flap 2100a or bends it back. The sealed tip breaks away and leaves a product outlet hole 2100b in the wall.

It may be seen from the Figures that the tip could be located in the wall beneath a flap and sealed to the flap in which case the outlet hole would remain in the wall when the flap was folded back and the tip would remain on the flap. It may also be seen that the flap may be bent from a corner as shown in FIGS. 56a–56c.

Another alternative embodiment is described in FIGS. 57a through 57d. This embodiment relates to an improved reclosable aperture forming means 2200 generally made of thermoformed plastic but not excluding plastic formed by other means or other formed materials. This improved unit 2200 does not require that a breakaway tip be broken away manually and/or disposed of. Instead, the improved unit 2200 embodies a system where a breakaway tip 2202, preferably reduced in height, has its uppermost surface 2204 sealingly attached to the upper inner surface 2206 of a cap member 2208. It may then be seen that the breakaway tip 2202 is automatically broken away from the lower formation 2210 at the fault line intersection 2212 of the tip 2202 and the upper surface 2214 of the lower formation 2210 when the cap 2208 is hinged up and away from its seat about said lower formation 2210. When the tip 2202 broken away from the lower formation 2210, an aperture or outlet 2216 is created. It may further be seen that the breakaway tip 2202 remains sealed to the inside of the cap 2208 which may be used normally to recap or open the aperture or outlet 2216 for dispensing or pouring out the contained product.

In its preferred embodiment, the breakaway tip 2202 should require a firm pull to break it away with an audible snap to insure the user that it was not tampered with. Break resistance is fully adjustable during manufacture. It can also be seen that the unit may be made of clear plastic so that the tip may be seen before broken away to show any evidence of tampering.

Figure 59A:
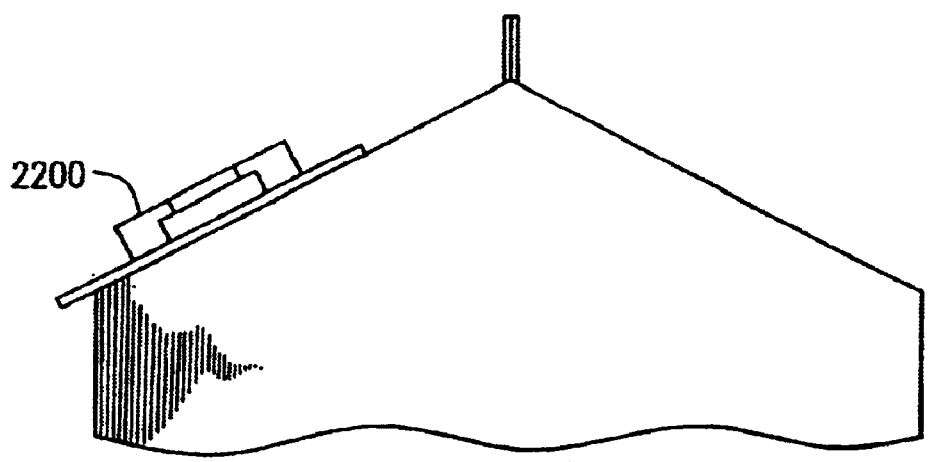
FIGS. 59a–59e disclose use of the reclosable aperture forming means in FIGS. 57a–57d on a container and a tube.
Figure 59B:
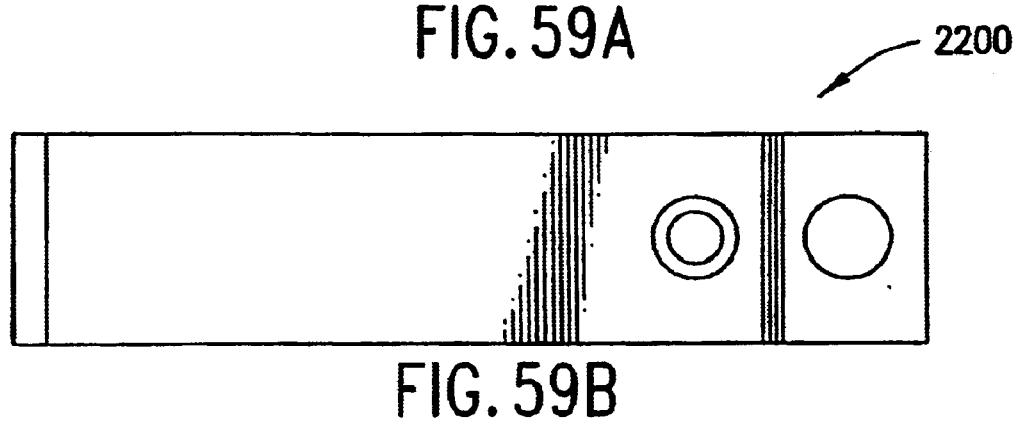
Figure 59C:
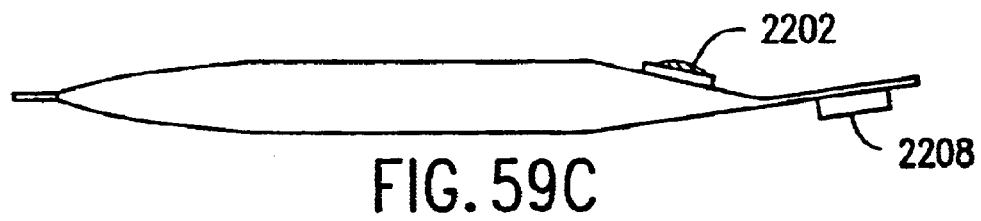
Figure 59D:
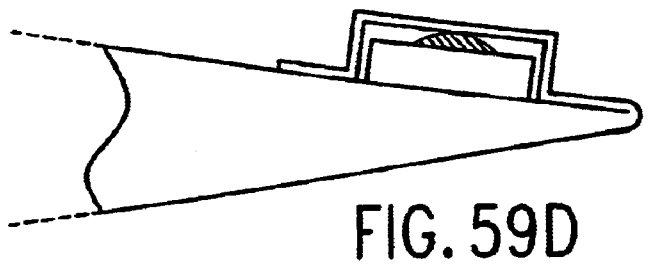
Figure 59E:
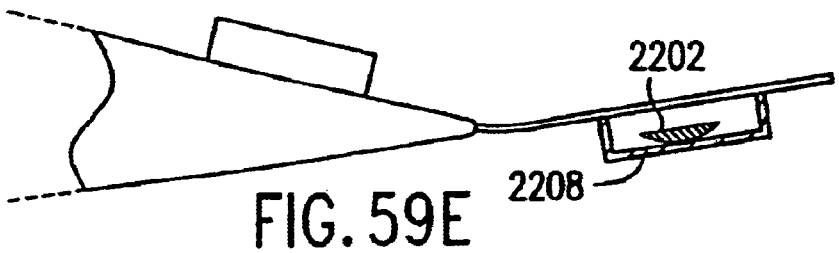

As illustrated in FIGS. 59A and 59B, to further insure tamper evidence, even though there will be a snap, at least one additional tacking point 2302 may be made between the flap 2310 containing the cap 2208 and the flat plastic around the lower breakaway tip protrusion to create a tamper evidence. These points can be highlighted by making a circular cut about them with a tiny uncut tab 2304. Thus, if the flap is even raised partially, it will tear the tiny tab and leave a hole in the flap. It will also be understood that various styles of finger grips 2306 may be used. One simple one is a round hole in the lower portion of the flap 2310.

As illustrated in FIGS. 59a to 59e, the reclosable aperture forming means 2200 can be used on, for example, a milk carton or a tube holding, for example, toothpaste or hair gel. Although the reclosable aperture forming means 2200 can be also used on other packages such as, for example, bags, containers, pouches, pillow packages (e.g. sachets), etc.

Figure 60A:
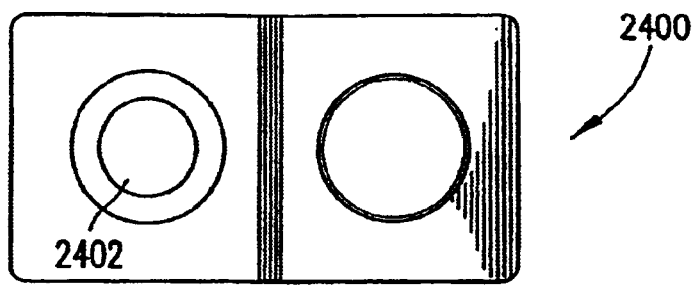
FIGS. 60a–60d disclose various views of another embodiment of a reclosable aperture forming means.
Figure 60B:
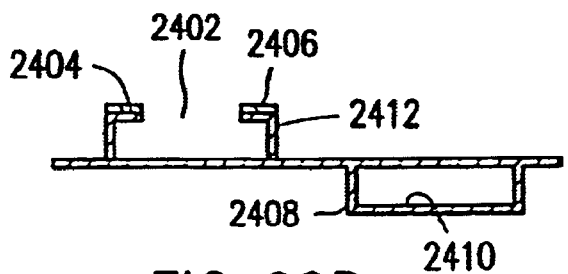
Figure 60C:
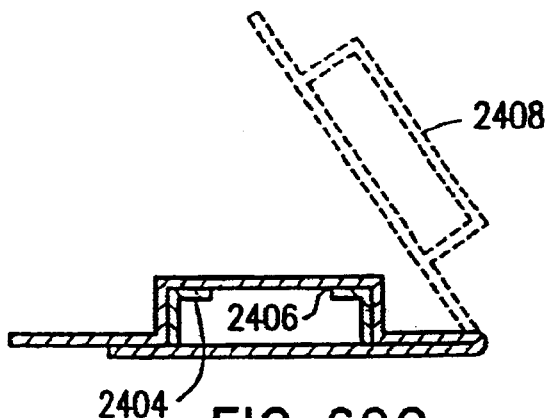
Figure 60D:
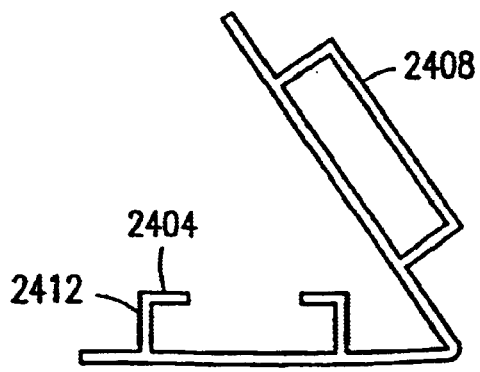
Figure 61A:
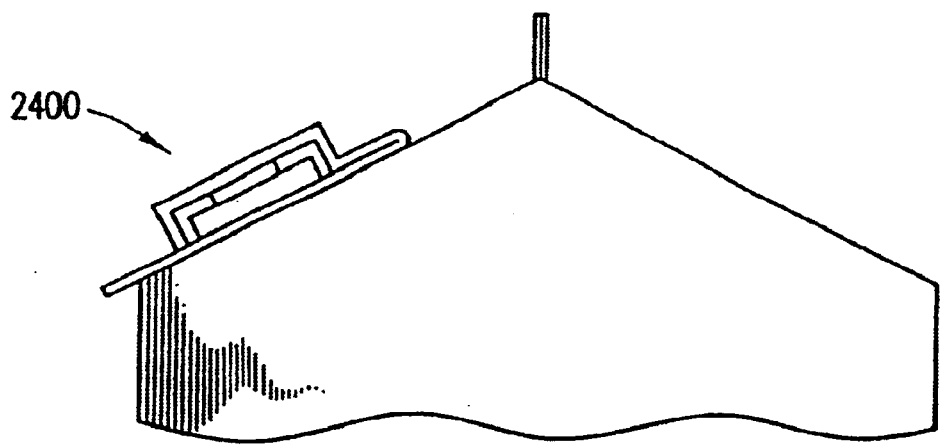
FIGS. 61a–61e disclose use of the reclosable aperture forming means in FIGS. 60a–60d on a container and a tube.
Figure 61B:
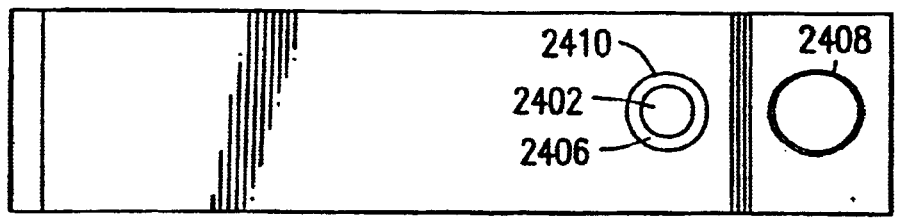
Figure 61C:
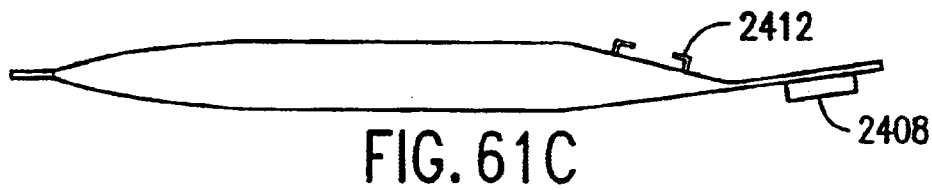
Figure 61D:
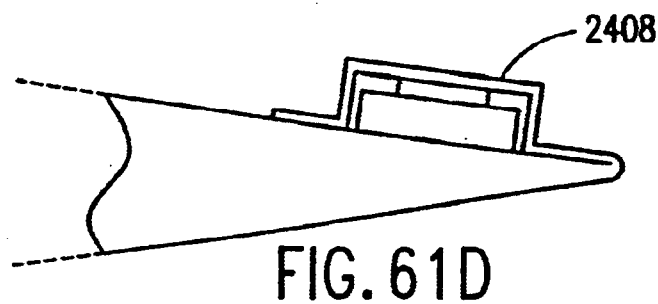
Figure 61E:
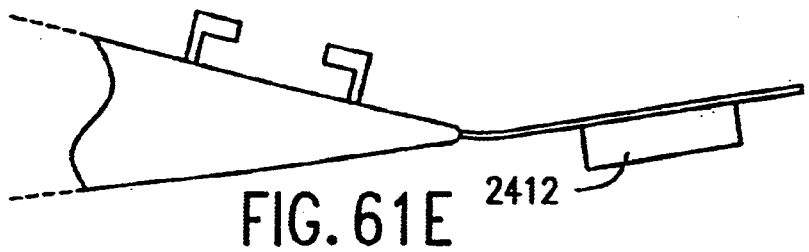

An alternative embodiment is described with reference to FIGS. 60a though 60d. The embodiment 2400 illustrated in FIGS. 60a through 60d replaces the breakaway tip 2202 formed in the upper surface 2214 of the lower drum 2412 shaped formation of FIGS. 57a through 57d with a preformed outlet hole 2402 at the center of the surface drum 2412 surrounded by a generally flat rim 2404 to which is applied a peelable adhesive 2406. The peelable adhesive 2406 may be heat sealable, although cold seal or pressure sensitive or other variety may be used. The hinged cap member 2408 formerly sealed to the breakaway tip may be peelably adhered to the rim 2404 surrounding the outlet hole 2402 to effectively seal off the outlet. When the hinged cap 2408 is hinged up it peels away from the drum formation 2412 by rupturing the adhesive 2406 and effectively opens the outlet hole 2402. This entire system, made of thermoformed plastic, can be either integrally formed into the wall of a container or sealingly attached to a container over a hole in the container wall.

It may also be seen that the inner top surface 2410 of the cap 2408 which covers the lower drum 2412 may have an adhesive applied to it rather than the rims 2404 and around the hole 2402. It may also be desirable to have the adhesive 2406 applied to the upper rim surface of the drum 2412 as well as the inner mating surface 2410 of the cap 2408. It may be seen that adhesive could be applied to the walls of the drum, however, it would be very difficult to rupture by hand. Since there is no longer a tip protrusion, the inner surface 2410 of the cap 2408 should be dimensioned so as to bring the adhesive into contact at the upper surface of the drum 2412.

As illustrated in FIGS. 61a to 61e, the reclosable aperture forming means 2400 can be used on, for example, a milk carton or a tube holding, for example, toothpaste or hair gel. Although the reclosable aperture forming means 2400 can be also used on other packages such as, for example, bags, containers, pouches, pillow packages (e.g. sachets), etc.

Figure 62A:
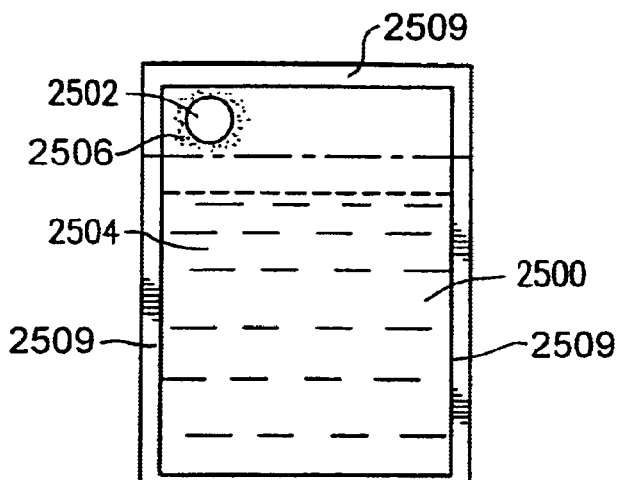
FIGS. 62A–62D disclose various views of another embodiment of an easy opening pouch.
Figure 62B:
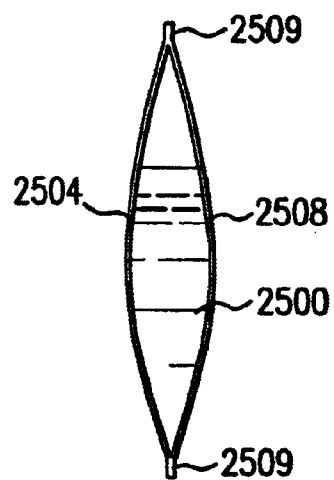
Figure 62C:
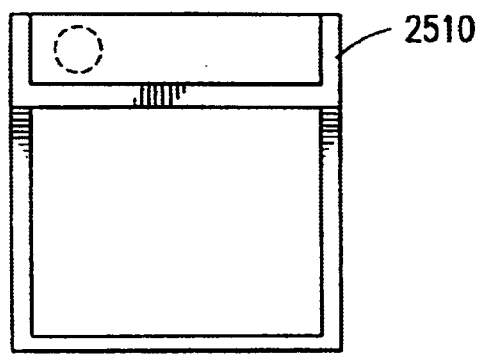
Figure 62D:
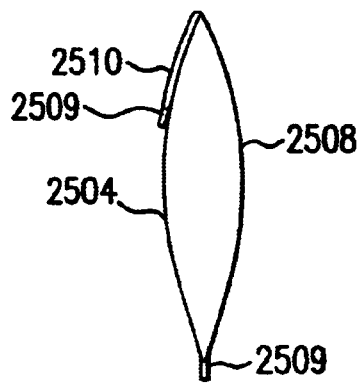
Figure 62E:
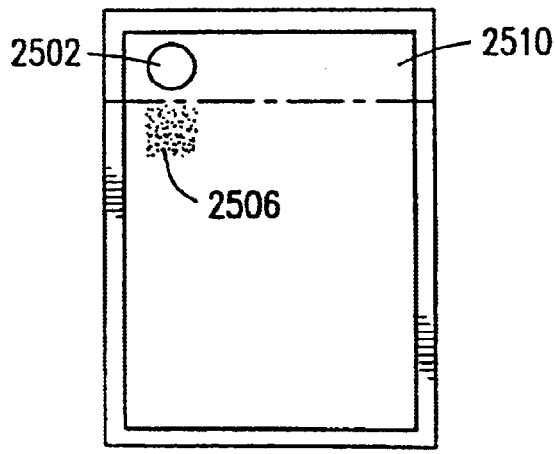
FIGS. 62E–62F illustrate an embodiment similar to that in FIGS. 62A–62D, with flap sealing adhesive in a different location.
Figure 62F:
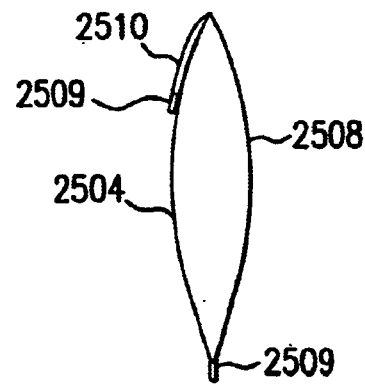
Figure 62G:
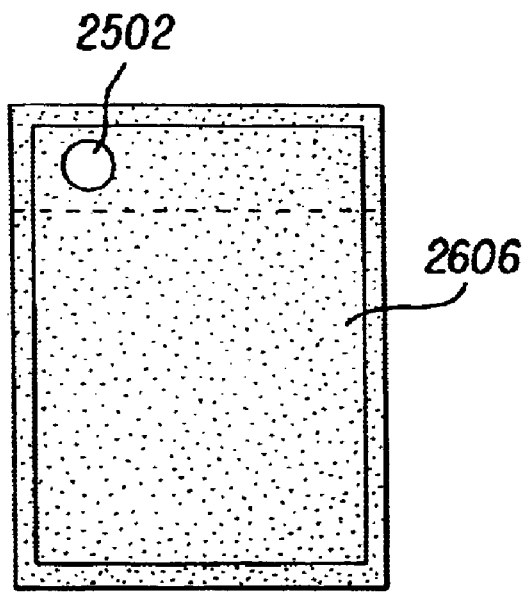
FIGS. 62G–62I illustrate an embodiment similar to those in FIGS. 62A–62F with a front film having a flap sealing layer on the entire front surface.
Figure 62H:
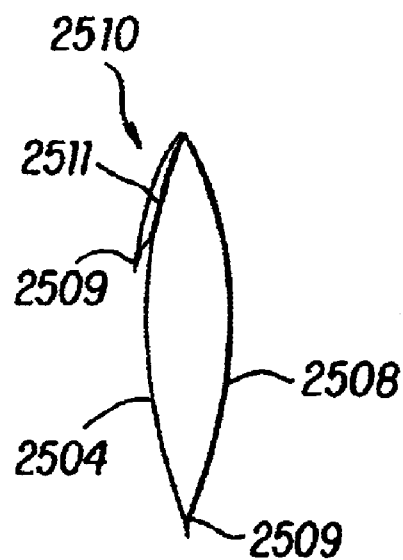
Figure 62I:
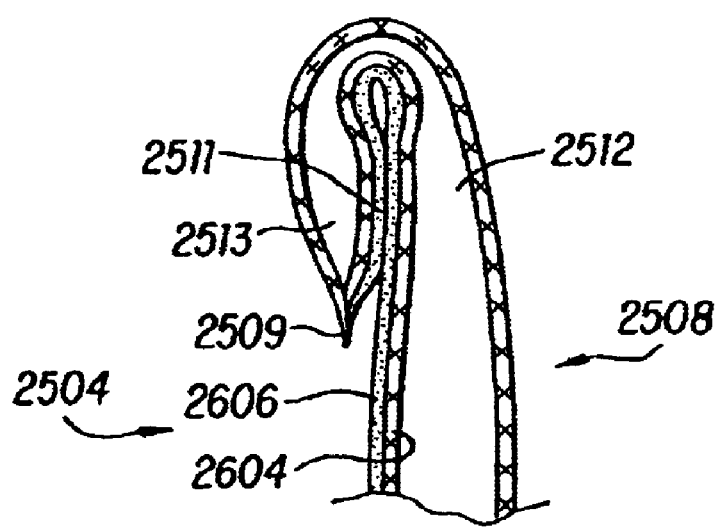
Figure 62J:
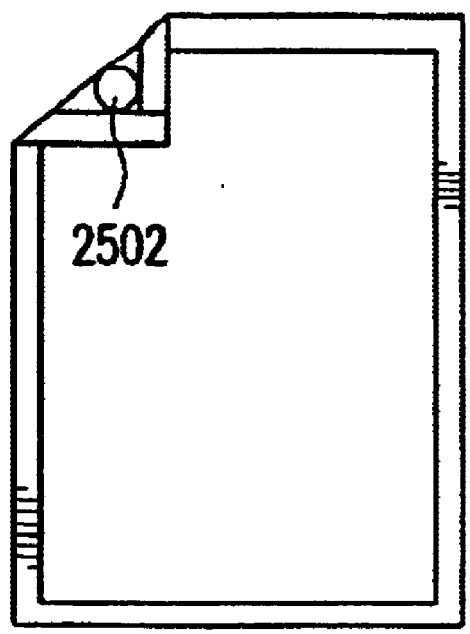
FIG. 62J illustrates an embodiment similar to those in FIGS. 62A–62I with the flap being corner folded.

Another alternative embodiment is described in FIGS. 62a through 62g. This embodiment relates to an easy opening rectangular pouch 2500 or other shape or form of packaging wherein a hole 2502 is created in one wall of film 2504 of the pouch etc. In the embodiment shown in FIG. 62a, the hole 2502 is at least encircled with a peelable adhesive 2506. The opposite wall of film 2508 is sealed to the side of film 2504 away from the adhesive 2506 (i.e., the side of the film 2504 on the inside or interior of the pouch) on all its edges to form edge seals 2509 to create a containment pouch. The containment pouch is then folded over to create a flap 2510 over the adhesive encircled hole 2502. The same surface of the wall of film 2504 that forms the inside of the flap 2510 (i.e., the surface of the film 2504 on the outside or exterior of the pouch) is then sealed by the peelable adhesive 2506 to its own surface. This surface is preferably heat sealed together but a contact or pressure adhesive may be used to eliminate the need for heat. The pouch 2500 may then be opened by lifting the flap 2510 which peels away from the surface of the wall 2504 containing the outlet hole 2502 to allow the outlet hole to be exposed to the outside. It is understood that the adhesive 2506 may be applied just around the hole 2502 and/or on the surface below the hole 2502 which the area around the hole 2502 touches when bent over or for convenience in manufacturing, the entire surface of the side of the pouch 2500 may be adhesive coated. An example of the alternative of having the adhesive 2506 on the surface below the hole 2502 which the area around the hole 2502 touches when bent over is illustrated in FIGS. 62e and 62f. An example of the alternative of having an adhesive layer on the entire surface of the side of the pouch 2500 is shown in FIGS. 62g, 62h and 62i. As shown in FIGS. 62g, 62h and 62i, the wall of film 2504 has a first layer, a product-facing layer 2604, on the inside or interior of the pouch and a second layer, a flap sealing layer 2606, on the outside or exterior of the pouch. The flap is folded over and the flap sealing layer 2606 is sealed to itself at flap sealing area 2511. The flap 2510 can also be a corner folded over such as, for example, the embodiment illustrated in FIG. 62j.

Figure 63:
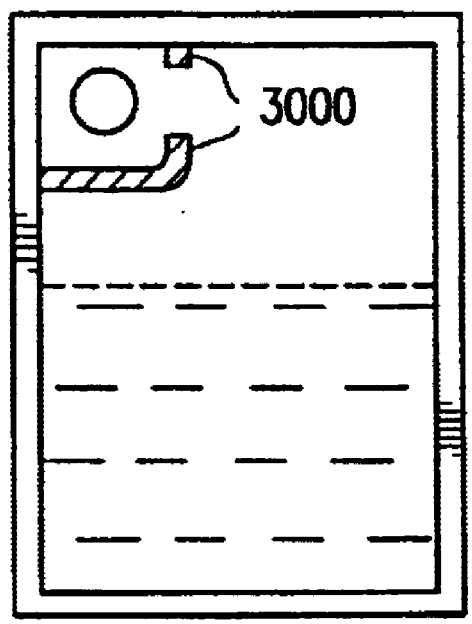
FIG. 63 discloses an easy opening pouch illustrating seals 3000 to control the product flow from the containment pocket.
Figure 68:
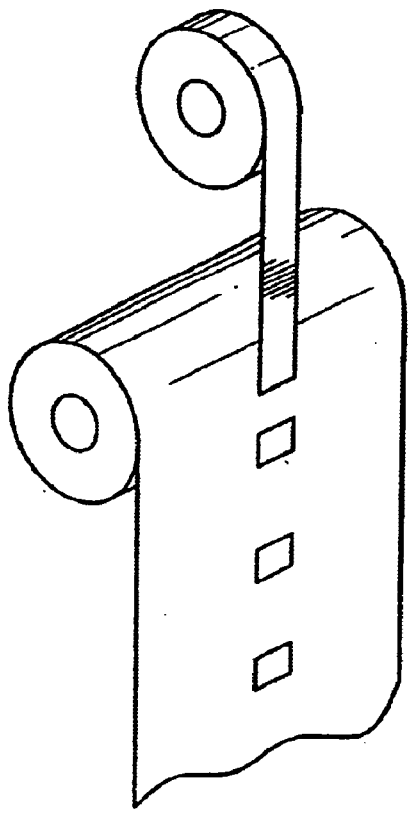
FIGS. 68 through 80 are illustrative examples of Redmond tubes, tube like packages and the reinforcement of breakaway tips.
Figure 69A:
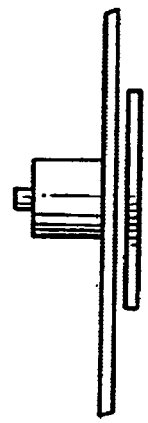
Figure 70A:
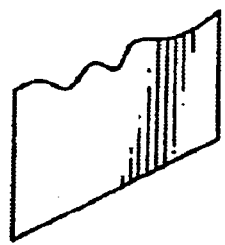
Figure 70B:
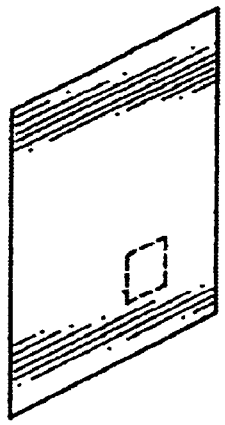
Figure 69:
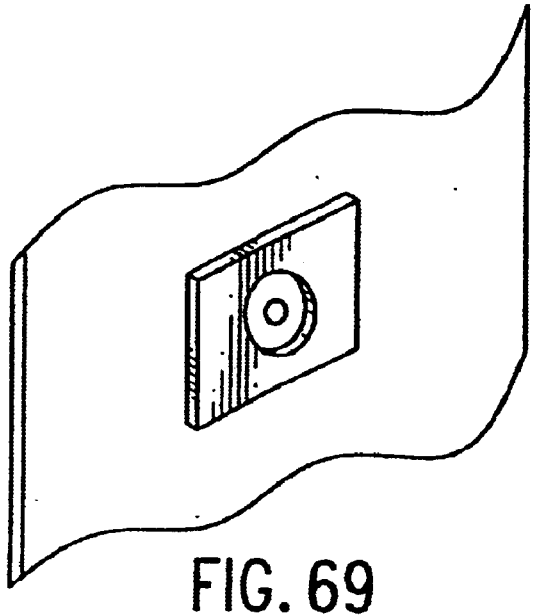
Figure 70C:
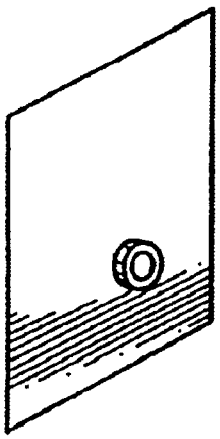
Figure 70G:
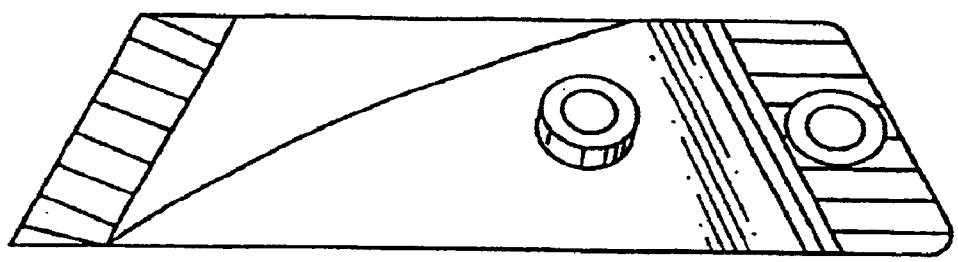
Figure 70F:
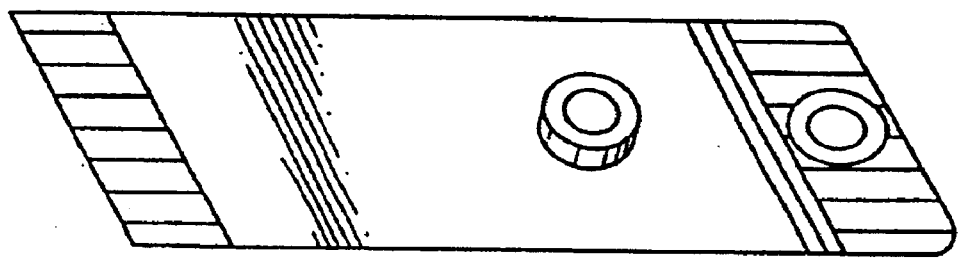
Figure 70E:
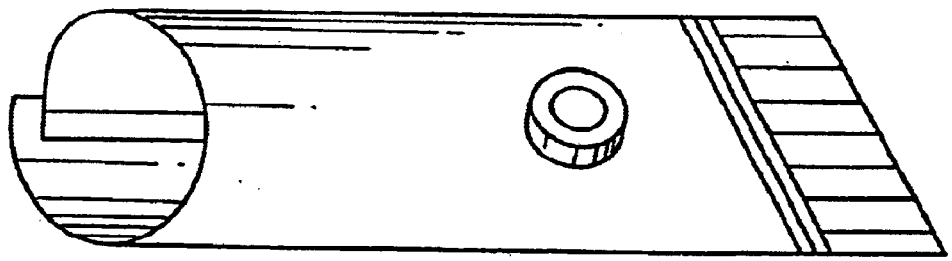
Figure 70D:
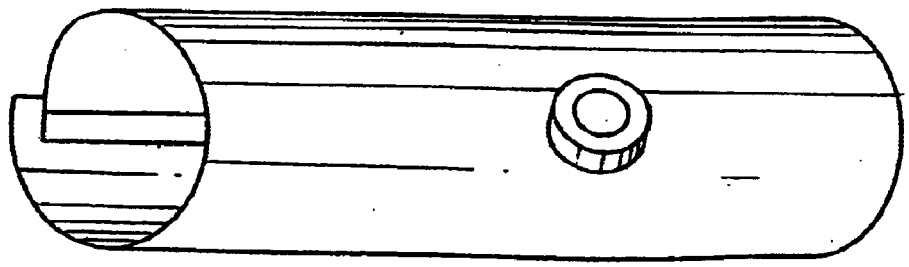
Figure 71:
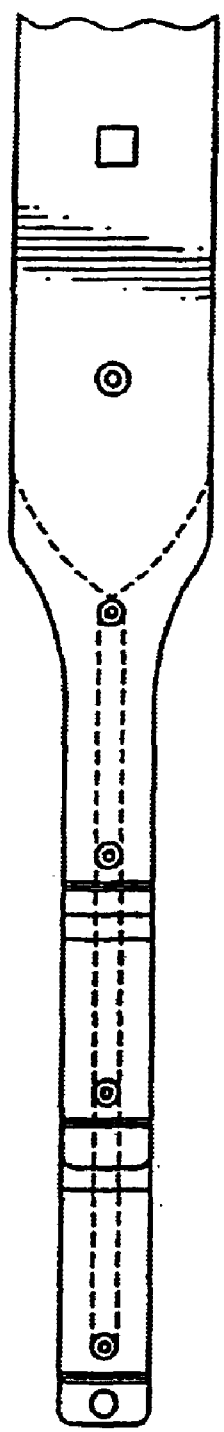
Figure 72:
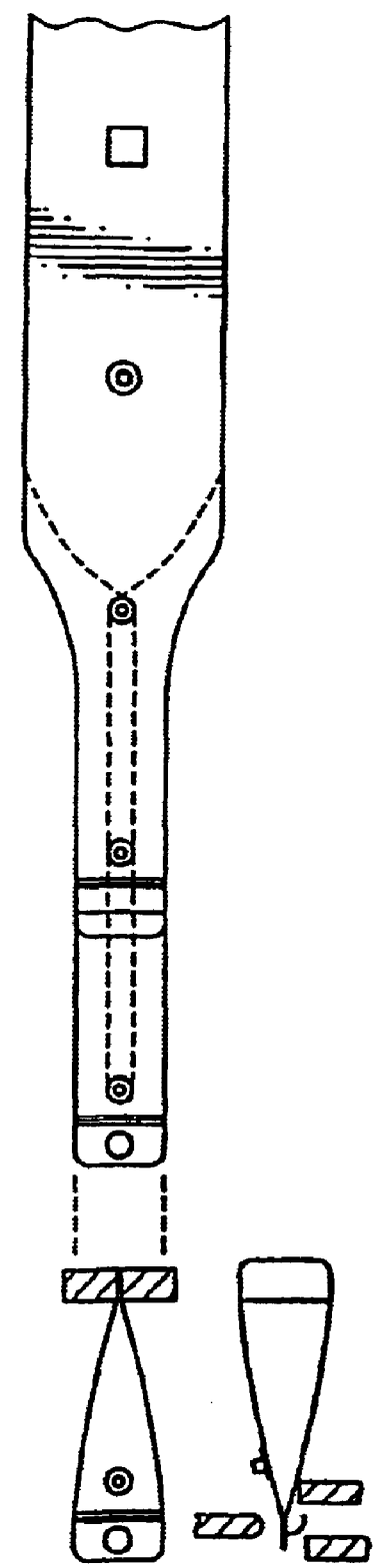
Figure 73:
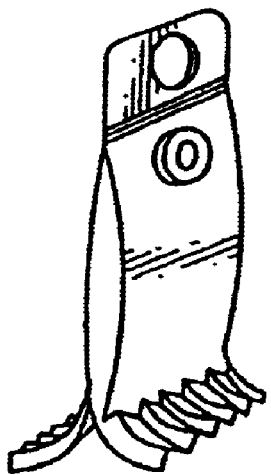
Figure 74:
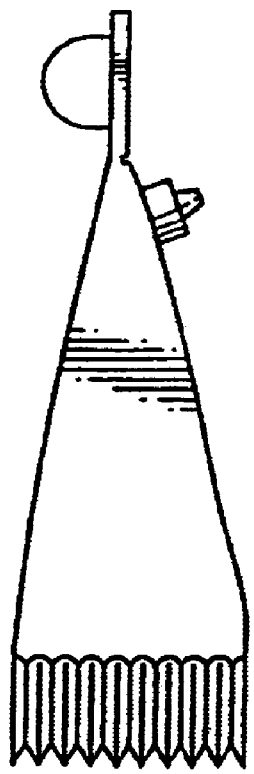
Figure 75:
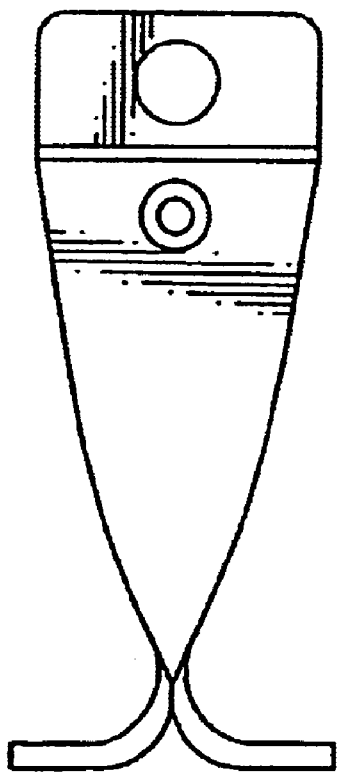
Figure 76:
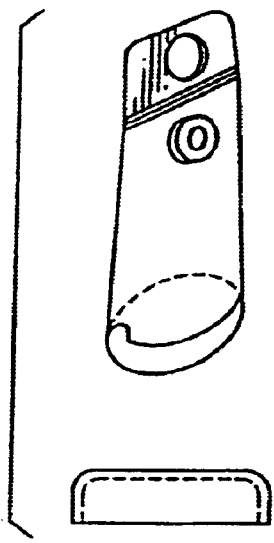
Figure 77:
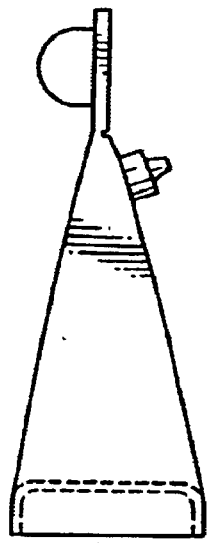
Figure 79:
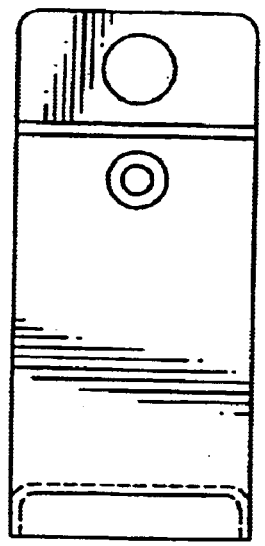
Figure 78:
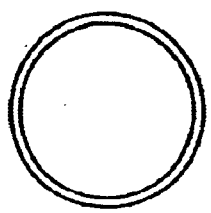
Figure 80:
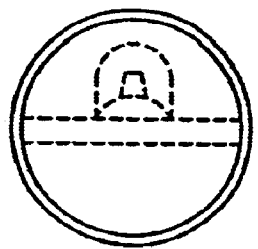

The purpose of the seals 3000 shown in FIG. 63 is to seal together the front and back walls of the pouch restricting the width of the flow channel of the low viscosity product. Not only is the channel width restricted but due to the nature of the films that form each wall, as the channel width is reduced the films that form each wall will not expand to allow product to flow between them without pressure. In other words a valving action may be produced wherein the product will not drip or spill out when no pressure is exerted on the body of the pouch. That is, the user must squeeze the pouch for product flow. When the user does not squeeze, there is no flow or drip. It will be realized that outlet hole diameters on the order of 0.030 inches may be required for low viscosity products.

An FIGS. 64a and 64b illustrate an easy opening rectangular pouch or other shape or form of packaging 3500 which has a fault line 3501 created in one wall or face of the pouch which at least partially encircles a portion of an area of a wall 3504 coated with peelable adhesive 3506. The end portion of said pouch or a corner or like part of said pouch is then folded over as shown in FIG. 65a to create a flap 3510 over the fault line partially encircled area of peelable adhesive. The surface of the wall 3504 that forms the inside of said flap 3510 is then sealed by the peelable adhesive to another location of its own surface at least within the confines of the area of adhesive encircled by the fault line. Either pressure sensitive or heat sealable adhesive may be used. The pouch may be opened by lifting the flap which tears out the fault line encircled adhesive together with the part of the wall it adhered to create an outlet aperture.

It may be seen that the peelable adhesive may extend beyond or outside of the at least partially encircling fault line but only the encircled wall area will be torn away to create the aperture.

It may also be seen that the outflow of product may be controlled by the additions of seals 3000 which extend in from the edge as in FIG. 63 of one of the drawings as well as seal patterns to create flow baffles. The flow control for the easy opening pouches, particularly for very low viscosity fluids such as, for example, soy sauce, skim milk, water, alcohol, solvents, or the like, comprise of at least one seal to block the rate of product flow from the containment pocket to the outlet hole.

Modern technology has developed laser systems which can put score or fault lines in very thin films. FIG. 64A is a top plan view of a peelable adhesive spot on the front face or wall of a pouch with a laser score line partially encircling a portion of the adhesive spot. FIG. 64B is an enlarged view of the peelable adhesive spot shown in FIG. 64 with a full circle score line. FIG. 65A illustrates the pouch shown in FIG. 64 in a frontal elevation with a portion of its top folded over into a flap which brings the encircled adhesive spot into contact with another part of the front face. FIG. 65B is a side view of the pouch shown in FIG. 65A. As shown in FIG. 65B, the pouch 3500 has a first wall or film 3504 with an inside surface 3504a and an outside surface 3504b and a second wall or film 3508 with an inside surface 3508*a* and an outside surface 3508*b*. As shown in FIG. 65B, the inside surface 3504*a* of first film 3504 is sealed to the inside surface 3508*a* of second film 3508 at edge seals 3509. To seal the flap 3510, the outside surface 3504*b* of the first film 3504 is sealed to its own surface at flap seal 3511. FIG. 65C is an enlarged view of the side view in FIG. 65B with encircled spot sealed to its own front face. As shown in FIGS. 65B and 65C, the sealing of the outside surface 3504*b* to itself at flap seal 3511 does not cause the inside surfaces 3504*a* and 3508*a* to seal together, as shown at unsealed areas 3512 and 3513. Similarly, as shown in FIG. 62*i*, the sealing of the flap sealing layer 2606 to itself at flap sealing area 2511 does not cause the product-facing layer 2604 of the first film 2504 on the inside of the package to seal to the second film 2508 on the inside of the package, as shown at unsealed areas 2512 and 2513. FIG. 66 illustrates an adhesive spot with a tongue shaped score line. FIG. 67 illustrates the tongue shaped outlet created after the top of the pouch is folded over to create a flap and adhesive is sealed to another part of the front face after which the flap is then raised to open the pouch.

FIGS. 68 through 78 are illustrative examples of Redmond tubes, tube like packages and the reinforcement of breakaway tips.

It will remain understood by those skilled in the art that the present invention in its broader aspects is not limited to the particular embodiments shown and described herein, and that variations may be made without departing from the principles of the invention and without sacrificing its chief advantages.

I claim:

1. A set of films for use in a dispensing package in the form of a pouch with a foldover flap to cover an outlet aperture, wherein the set of films comprises a first film and a second film;

wherein the first film comprises at least a product-facing layer and a flap sealing layer, the product-facing layer of the first film adapted to be located on the inside of the package, and the flap sealing layer of the first film adapted to be located on the outside of the package;

wherein the second film comprises at least a product-facing layer, the product-facing layer of the second film adapted to be located on the inside of the package;

wherein the product-facing layer of the first film is adapted to be sealed to the product-facing layer of the second film to form edge seals for the dispensing package;

wherein the flap sealing layer of the first film is adapted to be heat sealed to itself at a flap sealing temperature to seal a flap of the package; and wherein the product-facing layer of the first film and the product-facing layer of the second film that are adapted to be located on the inside of the package are also adapted such that they do not seal together at said flap sealing temperature.

2. A set of films as recited in claim 1, wherein the first film is comprised of plastic materials.

3. A set of films as recited in claim 2, wherein the first film is made by a process selected from the group of lamination and coextrusion.

4. A set of films as recited in claim 1, wherein said flap sealing layer of said first film covers an entire surface of the first film.

5. A multi-layer film for a wall of a pouch style containment package which comprises a flap folded over, wherein a surface of said multi-layer film heat seals to itself to form a flap seal to seal said flap, and wherein the sealing heat used to form said flap seal does not seal together any other surface of said pouch style containment package.

6. A multi-layer film as recited in claim 5, wherein the flap seal is a peelable seal.

* * * * *